US010111424B2

(12) United States Patent
Sahouani et al.

(10) Patent No.: US 10,111,424 B2
(45) Date of Patent: Oct. 30, 2018

(54) RELEASE OF BIOLOGICALLY ACTIVE AGENTS FROM POLYMERIC COMPOSITE PARTICLES

(71) Applicant: 3M INNOVATIVE PROPERTIES COMPANY, St. Paul, MN (US)

(72) Inventors: Hassan Sahouani, Hastings, MN (US); Mary M. Caruso Dailey, Maplewood, MN (US); Luke E. Heinzen, Mahtomedi, MN (US); Ibrahim A. El Hedok, Woodbury, MN (US)

(73) Assignee: 3M INNOVATIVE PROPERTIES COMPANY, Sa agent can be released from the polymeric composite particle by diffusing out of the porous polymeric core through the coating layer.

15 Claims, 3 Drawing Sheets

(51) Int. Cl.
| | |
|---|---|
| A01N 47/44 | (2006.01) |
| A01N 25/10 | (2006.01) |
| B01J 13/04 | (2006.01) |
| A01N 25/28 | (2006.01) |
| C08J 9/16 | (2006.01) |
| C08J 9/40 | (2006.01) |
| C08J 9/36 | (2006.01) |
| C08J 9/28 | (2006.01) |
| C08J 3/12 | (2006.01) |

(52) U.S. Cl.
CPC ............ A01N 51/00 (2013.01); B01J 13/043 (2013.01); C08J 3/126 (2013.01); C08J 9/16 (2013.01); C08J 9/286 (2013.01); C08J 9/365 (2013.01); C08J 9/40 (2013.01); C08J 2201/036 (2013.01); C08J 2201/04 (2013.01); C08J 2205/024 (2013.01); C08J 2207/10 (2013.01); C08J 2333/14 (2013.01); C08J 2347/00 (2013.01); C08J 2400/22 (2013.01); C08J 2491/06 (2013.01)

(56) References Cited

U.S. PATENT DOCUMENTS

| | | | |
|---|---|---|---|
| 4,303,736 | A | 12/1981 | Torobin |
| 4,661,577 | A | 4/1987 | Jo Lane |
| 4,690,825 | A | 9/1987 | Won |
| 4,743,545 | A | 5/1988 | Torobin |
| 4,806,360 | A | 2/1989 | Leong |
| 4,855,144 | A | 8/1989 | Leong |
| 4,923,894 | A | 5/1990 | Kanda |
| 5,026,890 | A | 6/1991 | Webb |
| 5,045,569 | A | 9/1991 | Delgado |
| 5,190,775 | A | 3/1993 | Klose |
| 5,214,119 | A | 5/1993 | Leir |
| 5,276,122 | A | 1/1994 | Aoki |
| 5,292,835 | A | 3/1994 | Jahns |
| 5,316,774 | A | 5/1994 | Eury |
| 5,461,134 | A | 10/1995 | Leir |
| 5,512,650 | A | 4/1996 | Leir |
| 5,554,686 | A | 9/1996 | Frisch, Jr. |
| 5,888,930 | A | 3/1999 | Smith |
| 5,908,896 | A | 6/1999 | Mayer |
| 6,013,286 | A | 1/2000 | Klose |
| 6,355,759 | B1 | 3/2002 | Sherman |
| 6,406,719 | B1 | 6/2002 | Farrar |
| 6,407,195 | B2 | 6/2002 | Sherman |
| 6,441,118 | B2 | 8/2002 | Sherman |
| 6,506,494 | B2 | 1/2003 | Brandys |
| 6,720,007 | B2 | 4/2004 | Walt |
| 6,746,684 | B2 | 6/2004 | Kitagaki |
| 6,835,397 | B2 | 12/2004 | Lee |
| 6,846,893 | B1 | 1/2005 | Sherman |
| 7,153,924 | B2 | 12/2006 | Kuepfer |
| 7,354,596 | B1 | 4/2008 | Banovetz |
| 7,371,464 | B2 | 5/2008 | Sherman |
| 7,491,409 | B1 | 2/2009 | Meers |
| 9,511,030 | B2 | 12/2016 | Oshima |
| 2003/0199633 | A1 | 10/2003 | Leon |
| 2005/0202096 | A1 | 9/2005 | Li |
| 2007/0148474 | A1 | 6/2007 | Leir |
| 2009/0068256 | A1 | 3/2009 | Meers |
| 2009/0176098 | A1 | 7/2009 | Masuda |
| 2009/0246279 | A1 | 10/2009 | Kong |
| 2010/0104647 | A1 | 4/2010 | Ting |
| 2011/0086100 | A1 | 4/2011 | Attia |
| 2011/0123456 | A1 | 5/2011 | Pandit |
| 2014/0309314 | A1 | 10/2014 | Sahouani |
| 2016/0068651 | A1 | 3/2016 | Sahouani |

FOREIGN PATENT DOCUMENTS

| | | |
|---|---|---|
| EP | 1947121 | 7/2008 |
| JP | H 07-053835 | 2/1995 |
| WO | WO 97/40103 | 10/1997 |
| WO | WO 01/54900 | 8/2001 |
| WO | WO 2006/133519 | 12/2006 |
| WO | WO 2007/146722 | 12/2007 |
| WO | WO 2009/061759 | 5/2009 |
| WO | WO 2012/082582 | 6/2012 |
| WO | WO 2012/134679 | 10/2012 |
| WO | WO 2012/142240 | 10/2012 |
| WO | WO 2013/077981 | 5/2013 |
| WO | WO 2013/166020 | 11/2013 |
| WO | WO 2015/094710 | 6/2015 |
| WO | WO 2015/095100 | 6/2015 |

OTHER PUBLICATIONS

Barrett, "The Determination of Pore Volume and Area Distributions in Porous Substances. I. Computations from Nitrogen Isotherms", J. Am. Chem. Soc., Jan. 1951, vol. 73, pp. 373-380.

Gokmen, "Porous polymer particles—A comprehensive guide to synthesis, characterization, functionalization and applications", Progress in Polymer Science, 2012, vol. 37, pp. 365-405.

Liang, "Synthesis of a Novel Porous Polymer/Ceramic Composite Material by Low-Temperature Atomic Layer Deposition", Chem. Mater., Oct. 2007, vol. 19, No. 22, pp. 5388-5394.

Stipanovic, "Microparticle Dispensers for the Controlled Release of Insect Pheromones", J. of Agricultural Food Chemistry, Apr. 2004, vol. 52, No. 8, pp. 2301-2308.

Castorwax®, Technical Data Sheet, Vertellus Performance Materials Inc., Greensboro, NC, USA, Nov. 2006, (1 page).

International Search Report for PCT International Application No. PCT/US2014/037799 dated Aug. 21, 2014, 3 pages.

10μm

500um

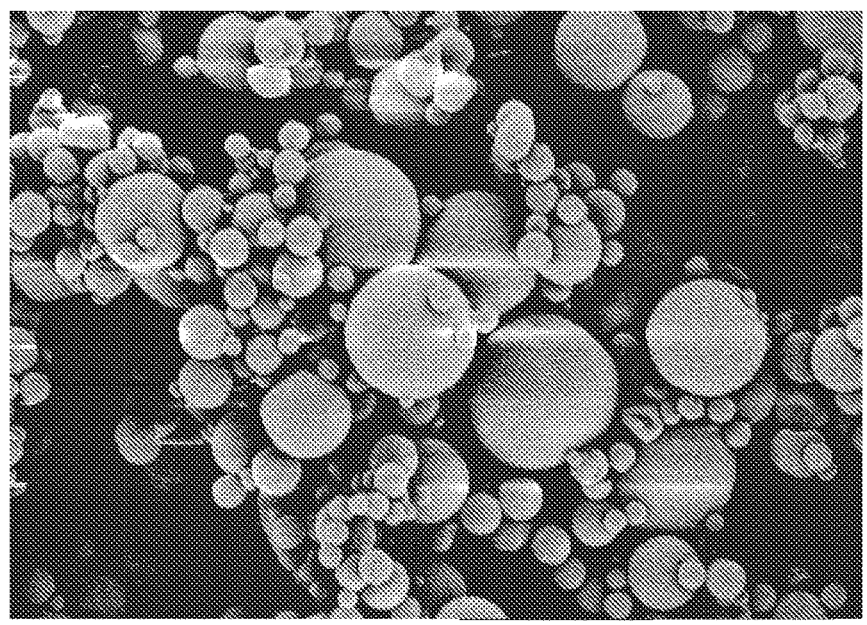
FIG. 3            12.0μm

RELEASE OF BIOLOGICALLY ACTIVE AGENTS FROM POLYMERIC COMPOSITE PARTICLES

CROSS REFERENCE TO RELATED APPLICATIONS

This application is a national stage filing under 35 U.S.C. 371 of PCT/US2014/037799, filed May 13, 2014, which claims priority to U. S. Provisional Application Nos. 61/990,348, filed May 8, 2014 and 61/824,412, filed May 17, 2013, the disclosures of which are incorporated by reference in their entireties herein.

FIELD

Polymeric composite particles are provided that can be used for the storage and delivery of various biologically active agents.

BACKGROUND

Methods for delivering biologically active agents are of great interest. Various particles have been developed for storage and delivery of various active agents. Some particles are inorganic as described, for example, in Patent Application Publication WO 2006/135519 A1 (Finnie et al.). Other particles have a polymeric shell surrounding a hollow core that can be filled with active agents. Such particles are described, for example, in U.S. Patent Application Publication 2010/0104647 A1 (Ting) and U.S. Patent Application Publication 2011/0123456 (Pandidt et al.). Still other particles are hydrogels that swell when placed in contact with an active agent. Such hydrogels are described, for example, in WO 2007/146722 (Wright et al.).

SUMMARY

Polymeric composite particles are provided that can be used for the storage and delivery of various biologically active agents. The polymeric composite particles contain a porous polymeric core and a coating layer around the porous polymeric core. The porous polymeric composite particles often further include a biologically active agent positioned within the porous polymeric core but not covalently bonded to the porous polymeric core. The biologically active agent can be released from the polymeric composite particle by diffusing out of the porous polymeric core through the coating layer.

In a first aspect, a polymeric composite particle is provided that includes a) a porous polymeric core, b) a biologically active agent positioned within the porous polymeric core, wherein the biologically active agent is not covalently bonded to the porous polymeric core, and c) a coating layer around the porous polymeric core, wherein the coating layer comprises a thermoplastic polymer, a wax, or a mixture thereof. The porous polymeric core contains a polymerized product of a reaction mixture that includes i) a first phase and ii) a second phase dispersed in the first phase, wherein a volume of the first phase is greater than a volume of the second phase. The first phase includes either 1) water and a polysaccharide dissolved in the water or 2) a surfactant and a compound of Formula (I)

(I)

where the variable n is an integer equal to at least 1. The second phase includes 1) a monomer composition comprising a first monomer of Formula (II)

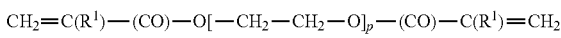

(II)

wherein p is an integer equal to at least 1 and $R^1$ is hydrogen or alkyl and 2) a poly(propylene glycol) having a weight average molecular weight of at least 500 grams/mole, wherein the poly(propylene glycol) is removed from the polymerized product to provide the porous polymeric core.

In a second aspect, a method of delivering a biologically active is provided. The method includes providing a polymeric composite particle as described above that includes a) a porous polymeric core, b) a biologically active agent positioned within the porous polymeric core, wherein the biologically active agent is not covalently bonded to the porous polymeric core, and c) a coating layer around the porous polymeric core, wherein the coating layer comprises a thermoplastic polymer, a wax, or a mixture thereof. The method further includes releasing the biologically active agent from the polymeric composite particle by diffusion through the coating layer.

BRIEF DESCRIPTION OF THE DRAWINGS

FIG. 3 is a scanning electron micrograph of the porous polymeric composite particles prepared in Example 4.

DETAILED DESCRIPTION

Figure 1A:
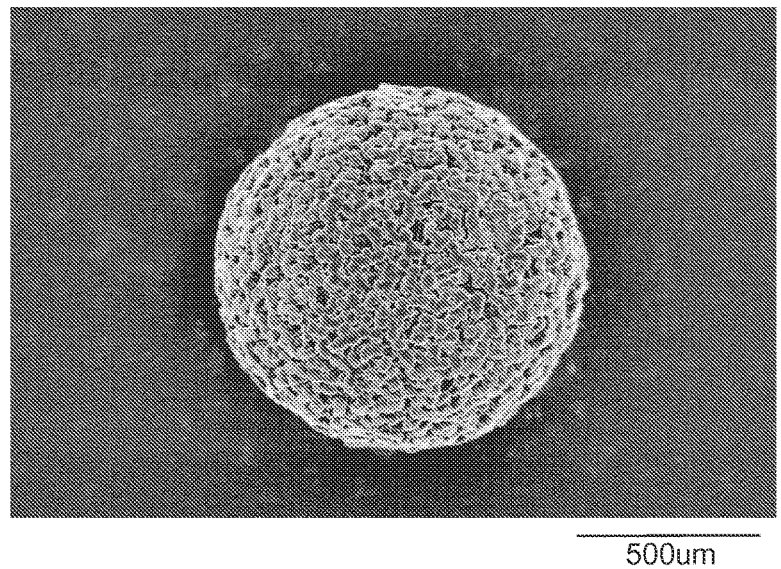
FIGS. 1A, 1B, and 1C are scanning electron micrographs of the porous polymeric core particles prepared in Preparatory Example 1. The three scanning electron micrographs differ in magnification.

Polymeric composite particles are provided that can be used for the storage and delivery of various biologically active agent. The polymeric composite particles contain a polymeric core and a coating layer around the polymeric core. The polymeric core of the polymeric composite particle is porous. That is, there are voids or free volume within the polymeric core. The polymeric core typically has pores on its outer surface and/or channels into the interior region. In at least some embodiments, the polymeric core is hollow. The terms "porous polymeric core", "porous polymeric core particle", "polymeric core", and "polymeric core particle" are used interchangeably. Because the polymeric composite particles include the porous polymeric core, the polymeric composite particles themselves can be considered to be porous. The terms "porous polymeric composite particle", "polymeric composite particle", and "composite particle" are used interchangeably.

The porous polymeric core particles containing biologically active agent (i.e., biologically active agents positioned or loaded within the porous polymeric core particles) can be referred to interchangeably as "loaded particles", "loaded core particles", "loaded polymeric core particles", and "loaded porous polymeric core particles". The biologically active agent is not covalently bonded to the polymeric core particles in the loaded polymeric core particles. Under suitable conditions, the biologically active agent can be released (i.e., delivered) from the loaded polymeric core particles and form the polymeric composite particles.

As used herein, the terms "polymer" and "polymeric", and "polymeric material" are used interchangeably to refer to a homopolymer, copolymer, terpolymer, or the like.

As used herein, the term "and/or" means one or both. For example, the expression thermoplastic polymer and/or wax refer to a thermoplastic polymer alone, a wax alone, or to both a thermoplastic polymer and a wax.

The coating layer around the porous polymeric particle contains a thermoplastic, wax, or mixture thereof. Both thermoplastic polymers and waxes soften when exposed to heat and return to their original forms when cooled to room temperature. The term "thermoplastic" is usually applied to synthetic polymeric materials but can also include naturally occurring polymeric materials having a molecular weight that is greater than most naturally occurring waxes. As used herein, the term "wax" refers to materials that have a lower molecular weight than the polymeric materials that are typically classified as thermoplastics. Waxes usually have at least one long alkyl chain (e.g., 4 to 24 carbon atoms) and are often classified as lipids. Some waxes are hydrocarbons (e.g., paraffin and polyethylene) while many natural waxes are esters of fatty acids and long chain alcohols (e.g., 4 to 24 carbon atoms). Because of the difference in molecular weight, waxes typically have a distinct melting point while thermoplastics have a glass transition temperature.

The porous polymeric core particle is typically formed from a reaction mixture that includes a first phase and a second phase dispersed in the first phase with the volume of the first phase being greater than a volume of the second phase. That is, the first phase can be considered to be the continuous phase and the second phase can be considered to be the dispersed phase within the continuous phase. The first phase provides a non-polymerizable medium for suspending the second phase as droplets within the reaction mixture. The second phase droplets include a monomer composition that can undergo polymerization plus a porogen, which is poly(propylene glycol).

Stated differently, the reaction mixture used to form the porous polymeric core particle includes a first phase comprising a non-polymerizable medium and a second phase suspended in the first phase as droplets. The second phase includes at least a monomer of Formula (II) plus poly (propylene glycol) of a suitable size to function as a porogen. The polymerized product is washed to remove the poly(propylene glycol) to provide the porous polymeric core particle.

The first phase of the reaction mixture typically includes either 1) water and a polysaccharide dissolved in the water or 2) a surfactant and a compound of Formula (I).

$$HO(-CH_2-CH(OH)-CH_2-O)_n-H \quad (I)$$

The variable n in Formula (I) is an integer equal to at least 1. The first phase is typically formulated to provide a suitable viscosity and volume for dispersion of the second phase as droplets within the first phase. If the viscosity of the first phase is too high, it can be difficult to provide the requisite shear to disperse the second phase. If the viscosity is too low, however, it can be difficult to suspend the second phase and/or to form polymeric cores that are relatively uniform and well separated from each other.

In some embodiments, the first phase contains a mixture of water and a polysaccharide dissolved in the water. The polysaccharide can be, for example, a water soluble starch or water soluble cellulose. Suitable water soluble starches and water soluble celluloses often have a viscosity in range of 6 to 10 centipoise for a 2 weight percent solution in water at room temperature (i.e., 20 to 25° C.). Water soluble starches are typically prepared by partial acid hydrolysis of starch. Examples of water soluble starches include those, for example, that are commercially available under the trade designation LYCOAT from Roquette (Lestrem, France). Examples of water soluble celluloses include, but are not limited to, alkyl cellulose (e.g., methyl cellulose, ethyl cellulose, ethyl methyl cellulose), hydroxylalkyl cellulose (e.g., hydroxymethyl cellulose, hydroxyethyl cellulose, hydroxypropyl cellulose, hydroxypropyl methyl cellulose, hdyroxyethyl methyl cellulose, hydroxyethyl ethyl cellulose), and carboxylalkyl cellulose (e.g., carboxymethyl cellulose).

In these embodiments, the first phase can contain up to 50 weight percent polysaccharide based on a total weight of the first phase. For example, the first phase can contain up to 40 weight percent, up to 30 weight percent, up to 25 weight percent, up to 20 weight percent, up to 15 weight percent, or up to 10 weight percent polysaccharide. The first phase typically includes at least 5 weight percent, at least 10 weight percent, or at least 15 weight percent polysaccharide. In some embodiments, the first phase contains 5 to 50 weight percent, 5 to 40 weight percent, 10 to 40 weight percent, 5 to 30 weight percent, 10 to 30 weight percent, 5 to 25 weight percent, 10 to 25 weight percent, or 15 to 25 weight percent polysaccharide based on a total weight of the first phase. The remainder of the first phase (i.e., the part of the first phase that is not a polysaccharide) is typically water or predominately water.

In some examples, the first phase contains 5 to 50 weight percent polysaccharide and 50 to 95 weight percent water, 5 to 40 weight percent polysaccharide and 60 to 95 weight percent water, 10 to 40 weight percent polysaccharide and 60 to 90 weight percent water, 5 to 30 weight percent polysaccharide and 70 to 90 weight percent water, 10 to 30 weight percent polysaccharide and 70 to 90 weight percent water, 5 to 25 weight percent polysaccharide and 75 to 95 weight percent water, 10 to 25 weight percent polysaccharide and 75 to 90 weight percent water, or 15 to 25 weight percent polysaccharide and 75 to 85 weight percent water. The percent weights are based on a total weight of the first phase. In many examples, the first phase includes only water and the dissolved polysaccharide. In other examples, the only other material included in the first phase is an optional organic solvent.

If an optional organic solvent is used in the water/polysaccharide first phase, the organic solvent selected to be miscible with water. Suitable organic solvents include, for example, an alcohol (e.g., methanol, ethanol, n-propanol, or isopropanol) or a polyol such as compound of Formula (I). The amounts of the optional organic solvent is usually no greater than 10 weight percent, no greater than 5 weight percent, or no greater than 1 weight percent based on the total weight of the first phase. In some examples, the first phase is free or substantially free of the optional organic solvent. As used herein with reference to the optional organic solvent in the first phase, the term "substantially free" means that an organic solvent is not purposely added to the first phase but may be present as an impurity in one of the other components in the first phase. For example, the amount of the optional organic solvent is less than 1 percent, less than 0.5 weight percent, or less than 0.1 weight percent based on a total weight of the first phase.

In other embodiments, the first phase contains a mixture of the compound of Formula (I) and a surfactant rather than a mixture of water and dissolved polysaccharide. For at least some second phase compositions, polymeric core particles having greater porosity (e.g., greater pore volume) can be obtained using a first phase that contains the compound of Formula (I) and a surfactant.

Suitable compounds of Formula (I) typically have a value of n that is in a range of 1 to 20, in a range of 1 to 16, in a range of 1 to 12, in a range of 1 to 10, in a range of 1 to 6, or in a range of 1 to 4. In many embodiments, the compound of Formula (I) is glycerol where the variable n is equal to 1. Other example compounds of Formula (I) are diglycerol (n is equal to 2), polyglycerol-3 (n is equal to 3), polyglycerol-4 (n is equal to 4), or polyglycerol-6 (n is equal to 6). The polyglycerols, which can be referred to as polyglycerins, are often a mixture of materials with varying molecular weight (i.e., materials with different values for n). Polyglycerols, diglycerol, and glycerol are commercially available, for example, from Solvay Chemical (Brussels, Belgium) and Wilshire Technologies (Princeton, N.J., USA).

A surfactant is typically used in combination with the compound of Formula (I) in the first phase. The surfactant is often a nonionic surfactant. The nonionic surfactant usually increases the porosity on the surface of the final polymeric particles. The first phase is often free or substantially free of an ionic surfactant that could interfere with the polymerization reaction of the monomers within the second phase. As used herein with reference to the ionic (i.e., anionic or cationic) surfactant, the term "substantially free" means that no ionic surfactant is purposefully added to the first phase but may be present as a trace impurity in one of the other components in the first phase. Any impurity is typically present in an amount no greater than 0.5 weight percent, no greater than 0.1 weight percent, or no greater than 0.05 weight percent based on a total weight of the first phase.

Any suitable nonionic surfactant can be used in the first phase. The nonionic surfactant often has one or more hydroxyl groups or ether linkages (e.g., —$CH_2$—O—$CH_2$—) in one portion of the molecule that can hydrogen bond with other components of the reaction mixture. Suitable nonionic surfactants include, but are not limited to alkyl glucosides, alkyl glucamides, alkyl polyglucosides, polyethylene glycol alkyl ethers, block copolymers of polyethylene glycol and polypropylene glycol, and polysorbates. Examples of suitable alkyl glucosides include, but are not limited to, octyl glucoside (also referred to as octyl-beta-D-glucopyranoside) and decyl glucoside (also referred to as decyl-beta-D-glucopyranoside). Examples of suitable alkyl glucamides include, but are not limited to, octanoyl-N-methylglucamide, nonanoyl-N-methylglucamide, and decanoyl-N-methylglucamide. These surfactants can be obtained, for example, from Sigma Aldrich (St. Louis, Mo., USA) or Spectrum Chemicals (New Brunswick, N.J., USA). Examples of suitable alkyl polyglucosides include, but are not limited to, those commercially available from Cognis Corporation (Cincinnati, Ohio, USA) under the trade designation APG (e.g., APG 325) and those commercially available from Dow Chemical (Midland, Mich., USA) under the trade designation TRITON (e.g., TRITON BG-10 and TRITON CG-110). Examples of polyethylene glycol alkyl ethers include, but are not limited to, those commercially available under the trade designation BRIJ (e.g., BRIJ 58 and BRIJ 98) from Sigma Aldrich (St. Louis, Mo., USA). Examples of block copolymers of polyethylene glycol and polypropylene glycol include, but are not limited to, those commercially available under the trade designation PLURONIC from BASF (Florham Park, N.J., USA). Examples of polysorbates include, but are not limited to, those commercially available under the trade designation TWEEN from ICI American, Inc. (Wilmington, Del., USA).

When the first phase contains a mixture of the compound of Formula (I) and a surfactant, the surfactant can be present in any suitable amount. Often, the surfactant is present in an amount equal to at least 0.5 weight percent, at least 1 weight percent, or at least 2 weight percent based on a total weight of the first phase. The surfactant can be present in an amount up to 15 weight percent, up to 12 weight percent, or up to 10 weight percent based on a total weight of the first phase. For example, the surfactant is often present in the first phase in an amount in a range of 0.5 to 15 weight percent, in a range of 1 to 12 weight percent, in a range of 0.5 to 10 weight percent, or in a range of 1 to 10 weight percent based on the total weight of the first phase. The remainder of the first phase (the part of the first phase that is not surfactant) typically is a compound of Formula (I) or predominately the compound of Formula (I).

In some examples, the first phase can contain 0.5 to 15 weight percent surfactant and 85 to 99.5 weight percent compound of Formula (I), 1 to 12 weight percent surfactant and 88 to 99 weight percent compound of Formula (I), 0.5 to 10 weight percent surfactant and 90 to 99.5 weight percent compound of Formula (I), or 1 to 10 weight percent surfactant and 90 to 99 weight percent compound of Formula (I). The percent weights are based on a total weight of the first phase. In many examples, the first phase contains only the surfactant and the compound of Formula (I). In other examples, the only other material included in the first phase is optional organic solvent or optional water.

When the first phase contains the compound of Formula (I) and a surfactant, an optional organic solvent that is miscible with the compound of Formula (I) can be present in the reaction mixture. Suitable organic solvents include, for example, an alcohol such as methanol, ethanol, n-propanol, or isopropanol. Additionally, optional water can be added to the first phase. The amount of any optional water or organic solvent is selected so that the desired viscosity of the first phase can be achieved. The amounts of the optional water or organic solvent is usually no greater than 10 weight percent, no greater than 5 weight percent, or no greater than 1 weight percent based on the total weight of the first phase. If higher amounts of water are included, the porosity may decrease. In some embodiments, the first phase is free or substantially free of the optional water or organic solvent. As used herein with reference to the optional water or organic solvent in the first phase, the term "substantially free" means that water or organic solvent is not purposely added to the first phase but may be present as an impurity in one of the other components in the first phase. For example, the amount of the optional water or organic solvent is less than 1 percent, less than 0.5 weight percent, or less than 0.1 weight percent based on a total weight of the first phase.

The reaction mixture includes a second phase dispersed in the first phase. The volume of the first phase is greater than the volume of the second phase. The volume of the first phase is sufficiently large compared to the volume of the second phase so that the second phase can be dispersed in the form of droplets within the first phase. Within each droplet, the monomer composition is polymerized to form a polymerized product. To form polymeric particles from the second phase, the volume ratio of the first phase to the second phase is typically at least 2:1. As the volume ratio increases (e.g., when the ratio is at least 3:1, at least 4:1, or at least 5:1), polymeric particles can be formed that have a relatively uniform size and shape. If the volume ratio is too large, however, the reaction efficiency is diminished (i.e., a smaller amount of polymeric particles are produced). The volume ratio is generally no greater than 25:1, no greater than 20:1, no greater than 15:1, or no greater than 10:1.

The second phase includes both a monomer composition plus a poly(propylene glycol) having a weight average molecular weight of at least 500 grams/mole. The polypropylene glycol functions as a porogen that gets partially entrained within the polymerized product as it is formed from the monomer composition. Because the polypropylene glycol has no polymerizable group, this material can be removed after formation of the polymerized product. Pores (i.e., void volume or free volume) are created when the previously entrained polypropylene glycol is removed. The polymeric core particles resulting from the removal of the entrained polypropylene glycol are porous. In at least some embodiments, these porous polymeric core particles have hollow centers. The presence of pores or the presence of both pores and hollow centers make the polymeric core particles well suited for storage and delivery of various biologically active agents.

The monomer composition within the second phase contains a first monomer of Formula (II)

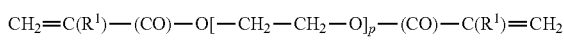

where the variable p is an integer equal to at least 1. In some embodiments, the variable p is an integer no greater than 30, no greater than 20, no greater than 16, no greater than 12, or no greater than 10. The number average molecular weight of the ethylene oxide portion of the monomer (i.e., the group —[CH$_2$CH$_2$—O]$_p$—) is often no greater than 1200 grams/mole (Daltons), no greater 1000 grams/mole, no greater than 800 grams/mole, mole, no greater than 600 grams/mole, no greater than 400 grams/mole, no greater than 200 grams/mole, or no greater than 100 grams/mole. The group R$^1$ is hydrogen or methyl. The monomer of Formula (II) in the second phase is typically not miscible with the first phase.

Suitable first monomers of Formula (II) are commercially available from Sartomer (Exton, Pa., USA) under the trade designation SR206 for ethylene glycol dimethacrylate, SR231 for diethylene glycol dimethacrylate, SR205 for triethylene glycol dimethacrylate, SR206 for tetraethylene glycol dimethacrylate, SR210 and SR210A for polyethylene glycol dimethacrylate, SR259 for polyethylene glycol (200) diacrylate, SR603 and SR344 for polyethylene glycol (400) di(meth)acrylate, SR252 and SR610 for polyethylene glycol (600) di(meth)acrylate, and SR740 for polyethylene glycol (1000) dimethacrylate.

In some embodiments, the first monomer of Formula (II) is the only monomer in the monomer composition of the second phase. In other embodiments, the first monomer of Formula (II) can be used in combination with at least one second monomer. The second monomer has a single ethylenically unsaturated group, which is often a (meth)acryloyl group of formula H$_2$C=CR$^1$—(CO)— where R$^1$ is hydrogen or methyl. Suitable second monomers usually are not miscible with the first phase but can be either miscible or not miscible with the first monomer of Formula (II).

Some example second monomers are of Formula (III).

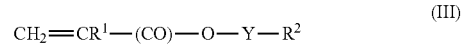

In this formula, group R$^1$ is hydrogen or methyl. In many embodiments, R$^1$ is hydrogen. Group Y is a single bond, alkylene, oxyalkylene, or poly(oxyalkylene). Group R$^2$ is a carbocyclic group or heterocyclic group. These second monomers tend to be miscible with the first monomer of Formula (I) in the second phase but are not miscible with the first phase.

As used herein, the term "alkylene" refers to a divalent group that is a radical of an alkane and includes groups that are linear, branched, cyclic, bicyclic, or a combination thereof. As used herein, the term "oxyalkylene" refers to a divalent group that is an oxy group bonded directly to an alkylene group. As used herein, the term "poly(oxyalkylene)" refers to a divalent group having multiple oxyalkylene units. Suitable Y alkylene and oxyalkylene groups typically have 1 to 20 carbon atoms, 1 to 16 carbon atoms, 1 to 12 carbon atoms, 1 to 10 carbon atoms, 1 to 8 carbon atoms, 1 to 6 carbon atoms, or 1 to 3 carbon atoms. The oxyalkylene is often oxyethylene or oxypropylene. Suitable poly(oxyalkylene) groups typically have 2 to 20 carbon atoms, 2 to 16 carbon atoms, 2 to 12 carbon atoms, 2 to 10 carbon atoms, 2 to 8 carbon atoms, 2 to 6 carbon atoms, or 2 to 4 carbon atoms. The poly(oxyalkylene) is often poly(oxyethylene), which can be referred to as poly(ethylene oxide) or poly(ethylene glycol).

Carbocyclic R$^2$ groups can have a single ring or can have multiple rings such as fused rings or bicyclic rings. Each ring can be saturated, partially unsaturated, or unsaturated. Each ring carbon atom can be unsubstituted or substituted with alkyl groups. Carbocyclic groups often has 5 to 12 carbon atoms, 5 to 10 carbon atoms, or 6 to 10 carbon atoms. Examples of carbocyclic groups include, but are not limited to, phenyl, cyclohexyl, cyclopentyl, isobornyl, and the like. Any of these carbocyclic groups can be substituted with an alkyl group having 1 to 20 carbon atoms, 1 to 10 carbon atoms, 1 to 6 carbon atoms, or 1 to 4 carbon atoms.

Heterocyclic R$^2$ groups can have a single ring or multiple rings such as fused rings or bicyclic rings. Each ring can be saturated, partially unsaturated, or unsaturated. The heterocyclic group contains at least one heteroatom selected from oxygen, nitrogen, or sulfur. The heterocyclic group often has 3 to 10 carbon atoms and 1 to 3 heteroatoms, 3 to 6 carbon atoms and 1 to 2 heteroatoms, or 3 to 5 carbon atoms and 1 to 2 heteroatoms. Examples of heterocyclic rings include, but are not limited to, tetrahydrofurfuryl.

Exemplary monomers of Formula (III) for use as the second monomer include, but are not limited to, benzyl (meth)acrylate, 2-phenoxyethyl (meth)acrylate (commercially available from Sartomer under the trade designation SR339 and SR340), isobornyl (meth)acrylate, tetrahydrofurfuryl (meth)acrylate (commercially available from Sartomer under the trade designation SR285 and SR203), 3,3,5-trimethylcyclohexyl (meth)acrylate (commercially available from Sartomer under the trade designation CD421 and CD421A), and ethoxylated nonyl phenol acrylate (commercially available from Sartomer under then trade designation SR504, CD613, and CD612).

Other example second monomers are alkyl (meth)acrylates of Formula (IV).

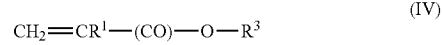

In Formula (IV), group $R^1$ is hydrogen or methyl. In many embodiments, $R^1$ is hydrogen. Group $R^3$ is a linear or branched alkyl having 1 to 20 carbon atoms, 1 to 10 carbon atoms, 1 to 6 carbon atoms, or 1 to 4 carbon atoms. These second monomers tend to be miscible with the first monomer of Formula (I) in the second phase but are not miscible with the first phase.

Examples of alkyl (meth)acrylates of Formula (IV) include, but are not limited to, methyl (meth)acrylate, ethyl (meth)acrylate, n-propyl (meth)acrylate, isopropyl (meth) acrylate, n-butyl (meth)acrylate, isobutyl (meth)acrylate, n-pentyl (meth)acrylate, 2-methylbutyl (meth)acrylate, n-hexyl (meth)acrylate, 4-methyl-2-pentyl (meth)acrylate, 2-ethylhexyl (meth)acrylate, 2-methylhexyl (meth)acrylate, n-octyl (meth)acrylate, isooctyl (meth)acrylate, 2-octyl (meth)acrylate, isononyl (meth)acrylate, isoamyl (meth) acrylate, n-decyl (meth)acrylate, isodecyl (meth)acrylate, 2-propylheptyl (meth)acrylate, isotridecyl (meth)acrylate, isostearyl (meth)acrylate, octadecyl (meth)acrylate, 2-octyldecyl (meth)acrylate, dodecyl (meth)acrylate, lauryl (meth) acrylate, and heptadecanyl (meth)acrylate.

In some embodiments, the only monomers in the monomer composition are the first monomer of Formula (II) and the second monomer of Formula (III), Formula (IV), or both. Any suitable amounts of the first monomer and second monomer can be used. The monomer composition often contains 10 to 90 weight percent of the first monomer and 10 to 90 weight percent of the second monomer based on a total weight of monomers in the monomer composition. For example, the second phase can contain 20 to 80 weight percent of the first monomer and 20 to 80 weight percent of the second monomer, 25 to 75 weight percent of the first monomer and 25 to 75 weight percent of the second monomer, 30 to 70 weight percent of the first monomer and 30 to 70 weight percent of the second monomer, or 40 to 60 weight percent of the first monomer and 40 to 60 weight percent of the second monomer based on a total weight of monomers in the monomer composition.

Depending on the particular biologically active agent that will be positioned within the polymeric core particle, it can be desirable to include at least one hydrophilic second monomer in the monomer composition. The addition of a hydrophilic second monomer tends to make the polymeric core particles more suitable for storage and delivery of hydrophilic biologically active agents. Hydrophilic second monomers are selected so that they are not miscible with the first phase. These monomers may or may not be miscible with the first monomer of Formula (II).

Some example hydrophilic second monomers are hydroxyl-containing monomers of Formula (V).

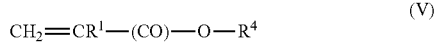

(V)

In Formula (V), group $R^1$ is hydrogen or methyl. In many embodiments, $R^1$ is hydrogen. Group $R^4$ is an alkyl substituted with one or more hydroxyl groups or a group of formula $-(CH_2CH_2O)_q CH_2CH_2OH$ where q is an integer equal to at least 1. The alkyl group typically has 1 to 10 carbon atoms, 1 to 6 carbon atoms, 1 to 4 carbon atoms, or 1 to 3 carbon atoms. The number of hydroxyl groups is often in a range of 1 to 3. The variable q is often in a range of 1 to 20, in a range of 1 to 15, in a range of 1 to 10, or in a range of 1 to 5. In many embodiments, the second monomer of Formula (IV) has a single hydroxyl group.

Example monomers of Formula (V) include, but are not limited to, 2-hydroxyethyl (meth)acrylate, 2-hydroxypropyl (meth)acrylate, 3-hydroxypropyl (meth)acrylate, and 4-hydroxybutyl (meth)acrylate), 2-hydroxylbutyl (meth)acrylate, polyethylene glycol mono(meth)acrylate (e.g., monomers commercially available from Sartomer (Exton, Pa., USA) under the trade designation CD570, CD571, and CD572), and glycol mono(meth)acrylate.

Other example hydrophilic second monomers are hydroxyl-containing monomers of Formula (VI).

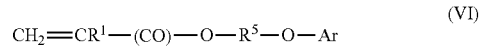

(VI)

In Formula (VI), group $R^1$ is hydrogen or methyl. In many embodiments, $R^1$ is hydrogen. Groups $R^5$ is an alkylene substituted with at least one hydroxyl group. Suitable alkylene groups often have 1 to 10 carbon atoms, 1 to 6 carbon atoms, or 1 to 4 carbon atoms. The alkylene group $R^5$ can be substituted with 1 to 3 hydroxyl groups but is often substituted with a single hydroxyl group. The group Ar is an aryl group having 6 to 10 carbon atoms. In many embodiments, the Ar group is phenyl. One example monomer of Formula (VI) is 2-hydroxy-2-phenoxypropyl (meth)acrylate.

If the second monomer is of Formula (V) or (VI), which are hydroxyl-containing monomers, the amount of this monomer that can be combined with the first monomer of Formula (II) is often no greater than 2 weight percent based on a total weight of monomers in the monomer composition. If greater than about 2 weight percent of the second monomer of Formula (V) or (VI) is used, the resulting polymeric particles tend to have diminished porosity.

Other hydrophilic monomers can be used as the second monomers in larger quantities than the second monomers of Formula (V) or (VI) without diminishing the porosity of the resulting polymeric core particles. For example, sulfonyl-containing monomers of Formula (VII) or a salt thereof can be included in the monomer composition along with the first monomer of Formula (II).

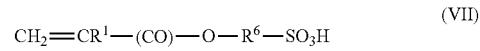

(VII)

In Formula (VII), group $R^1$ is hydrogen or methyl. In many embodiments, $R^1$ is hydrogen. Group $R^6$ is an alkylene having 1 to 10 carbon atoms, 1 to 6 carbon atoms, or 1 to 4 carbon atoms. Examples of sulfonyl-containing monomers of Formula (VII) include, but are not limited to, sulfoethyl (meth)acrylate and sulfopropyl (meth)acrylate. The sulfonyl-containing monomers can be salts under some pH conditions. That is, monomer can have a negative charge and be associated with a positively charged counter ion. Example counter ions include, but are not limited to, alkali metals, alkaline earth metals, ammonium ions, and tetraalkyl ammonium ions.

If the second monomer is a sulfonyl-containing monomer of Formula (VII), the monomer composition can contain up to 20 weight percent of this monomer based on a total weight of monomers in the monomer composition. In some embodiments, the only monomers in the monomer composition are the first monomer of Formula (II) and the second monomer of Formula (VII). Any suitable amounts of the first monomer and second monomer can be used. The monomer composition often contains 80 to 99 weight percent of the first monomer of Formula (II) and 1 to 20 weight percent of the second monomer of Formula (VII) based on a total weight of monomers in the monomer composition. For example, the monomer composition can contain 85 to 99 weight percent of the first monomer and 1 to 15 weight percent of the second monomer, 90 to 99 weight percent of the first monomer and 1 to 10 weight percent of the second monomer, and 95 to 99 weight percent of the first monomer and 1 to 5 weight percent of the second monomer based on a total weight of monomers in the monomer composition.

In other embodiments, the monomer composition includes a first monomer of Formula (II) and two second monomers, which are a sulfonyl-containing monomer, such as those of Formula (VII), and a hydroxyl-containing monomer, such as those of Formula (V) or (VI). When the hydroxyl-containing monomer is combined with a sulfonyl-containing monomer, higher amounts of the hydroxyl-containing monomer can be added to the monomer composition without substantially decreasing the porosity of the resulting polymeric particles. That is, the amount of the hydroxyl-containing monomer can be greater than 2 weight percent based on the weight of the monomers in the monomer composition. Such monomer composition often contains 80 to 99 weight percent of the first monomer of Formula (II) and 1 to 20 weight percent of the second monomer, wherein the second monomer is a mixture of the sulfonyl-containing monomer and the hydroxyl-containing monomer. Up to 50 weight percent, up to 40 weight percent, up to 20 weight percent, or up to 10 weight percent of the second monomer can be the hydroxyl-containing monomer.

In still other embodiments, the monomer composition includes a first monomer of Formula (II) and two second monomers, which are a sulfonyl-containing monomer, such as those of Formula (VII), and a monomer of Formula (III). Such monomer compositions often contain 1 to 20 weight percent of the monomer of Formula (VII) and 80 to 99 weight percent of a mixture of the monomer of Formula (II) and the monomer of Formula (III). For example, the monomer compositions can contain 1 to 10 weight percent of the monomer of Formula (VII) and 90 to 99 weight percent of a mixture of the monomer of Formula (II) and the monomer of Formula (III) or can contain 1 to 5 weight percent of the monomer of Formula (VII) and 95 to 99 weight percent of a mixture of the monomer of Formula (II) and the monomer of Formula (III). These compositions can be advantageous because they can be used to load either hydrophobic or hydrophilic biologically active agents.

In some more specific examples, the monomer composition can contain 1 to 20 weight percent of the monomer of Formula (VII), 1 to 98 weight percent of the monomer of Formula (II), and 1 to 98 weight percent of the monomer of Formula (III). In another example, the monomer composition can contain 1 to 20 weight percent of the monomer of Formula (VII), 5 to 95 weight percent of the monomer of Formula (II), and 5 to 95 weight percent of the monomer of Formula (III). In another example, the monomer composition contains 1 to 10 weight percent of the monomer of Formula (VII), 20 to 80 weight percent of the monomer of Formula (II), and 20 to 80 weight percent of the monomer of Formula (III). In yet another example, the monomer composition contains 1 to 10 weight percent of the monomer of Formula (VII), 30 to 70 weight percent of the monomer of Formula (II), and 30 to 70 weight percent of the monomer of Formula (III). In still another example, the monomer composition contains 1 to 10 weight percent of the monomer of Formula (VII), 40 to 60 weight percent of the monomer of Formula (II), and 40 to 60 weight percent of the monomer of Formula (III).

In these monomer compositions containing the monomers of Formulas (VII), (II), and (III), the amount of the monomer of Formula (VII) can be used to control the average size of the porous polymeric core particle. For example, when about 5 weight percent of the monomer of Formula (VII) is included in the monomer composition, the resulting porous polymeric core particles have an average diameter of approximately 10 micrometers. When about 1 weight percent of the monomer of Formula (VII) is included in the monomer composition, the resulting porous polymeric core particles have an average diameter of approximately 3 micrometers.

Still other example second monomers are carboxyl-containing monomers that have a carboxylic acid group (—COOH) or salt thereof. Examples of these carboxyl-containing monomers include, but are not limited to, (meth)acrylic acid and carboxyalkyl (meth)acrylates such as 2-carboxyethyl (meth)acrylate, 3-carboxypropyl (meth)acrylate, and the like. The carboxyl-containing monomers can be salts under some pH conditions. That is, these monomer can have a negative charge and be associated with a positively charged counter ion. Example counter ions include, but are not limited to, alkali metals, alkaline earth metals, ammonium ions, and tetraalkyl ammonium ions.

Yet other second monomers are quaternary ammonium salts such as, for example, (meth)acrylamidoalkyltrimethylammonium salts (e.g., 3-methacrylamidopropyltrimethylammonium chloride and 3-acrylamidopropyltrimethylammonium chloride) and (meth)acryloxyalkyltrimethylammonium salts (e.g., 2-acryloxyethyltrimethylammonium chloride, 2-methacryloxyethyltrimethylammonium chloride, 3-methacryloxy-2-hydroxypropyltrimethylammonium chloride, 3-acryloxy-2-hydroxypropyltrimethylammonium chloride, and 2-acryloxyethyltrimethylammonium methyl sulfate).

In addition to the first monomer of Formula (II) or to a mixture of the first monomer of Formula (II) and one or more of the second monomers described above, the monomer composition can optionally contain a third monomer with at least two polymerizable groups. The polymerizable groups are typically (meth)acryloyl groups. In many embodiments, the third monomer has two or three (meth)acryloyl groups. The third monomer typically is not miscible with the first phase and may or may not be miscible with the first monomer of Formula (II).

Some third monomers have a hydroxyl group. Such monomers can function as crosslinkers like the first monomer of Formula (II) but can provide polymeric particles with increased hydrophilic character. This can be desirable for the storage and delivery of hydrophilic active agents. An example hydroxyl-containing third monomer is glycerol di(meth)acrylate.

Some third monomers are selected to have at least three polymerizable groups. Such third monomers can be added to provide more rigidity to the resulting polymeric particles. The addition of these third monomers tends to minimize swelling of the polymeric particles when exposed to an active agent or when exposed to moisture. Suitable third monomers include, but are not limited to, ethoxylated trimethylolpropane tri(meth)acrylates such as ethoxylated (15) trimethylolpropane triacrylate (commercially available under the trade designation SR9035 from Sartomer) and ethoxylated (20) trimethylolpropane triacrylate (commercially available under the trade designation SR415 from Sartomer); propoxylated trimethylolpropane tri(meth)acrylates such as propoxylated (3) trimethylolpropane triacrylate (commercially available under the trade designation SR492 from Sartomer) and propoxylated (6) trimethylolpropane triacrylate (commercially available under the trade designation CD501 from Sartomer); tris(2-hydroxyethyl) isocyanurate tri(meth)acrylates such as tris(2-hydroxyethyl) isocyanurate triacrylate (commercially available under the trade designations SR368 and SR368D from Sartomer); and propoxylated glyceryl tri(meth)acrylates such as propoxylated (3) glycerol triacrylate (commercially available under the trade designation SR9020 and SR9020HP from Sartomer).

When a third monomer is present in the monomer composition, any suitable amount can be used. The third monomer is often used in an amount up to 20 weight percent based on the total weight of monomers in the monomer composition. In some embodiments, the amount of the third monomer is up to 15 weight percent, up to 10 weight percent, or up to 5 weight percent.

The monomer composition often contains 10 to 100 percent of the first monomer, 0 to 90 weight percent of the second monomer, and 0 to 20 weight percent of the third monomer based on a total weight of monomers in the monomer composition. For example, the monomer composition can contain 10 to 90 weight percent of the first monomer, 10 to 90 weight percent of the second monomer, and 0 to 20 weight percent of the third monomer. The monomer composition can contain 10 to 89 weight percent of the first monomer, 10 to 89 weight percent of the second monomer, and 1 to 20 weight percent of the third monomer based on a total weight of the monomer composition.

In addition to the monomer composition, the second phase contains poly(propylene glycol), which functions as a porogen. The poly(propylene glycol) is soluble in the monomer composition within the second phase but is dispersible within the first phase. Stated differently, the poly(propylene glycol) is completely miscible with the second phase and partially miscible with the first phase. The poly(propylene glycol) is removed after polymerization of the monomer composition to provide pores (e.g., void volumes or free volumes) in the polymeric core particle. The poly(propylene glycol) does not have any polymerizable groups (i.e., it is not a monomer) and, in general, is not covalently attached to the polymeric core particles that forms within the second phase. It is believed that some of the poly(propylene glycol) may become entrained within the polymerized product. The removal of the entrained poly(propylene glycol) can result in the formation of hollow polymeric core particles. It is further believed that some of the poly(propylene glycol) may be positioned on the interface between the first phase and the second phase as the polymerized product is formed in the second phase. The presence of the poly(propylene glycol) at the surface of the forming polymerized product may result in the formation of a polymeric particles having surface porosity. The surface porosity can be seen from electron micrographs of the polymeric particles such as in FIGS. 1A, 1B, and 1C.

Any suitable molecular weight of poly(propylene glycol) can be used as the porogen. The molecular weight can affect the size of the pores that are formed in the polymeric core particles. That is, the pore size tends to increase with the molecular weight of the poly(propylene glycol). The weight average molecular weight is often at least 500 grams/mole, at least 800 grams/mole, or at least 1000 grams/mole. The weight average molecular weight of the poly(propylene glycol) can be up to 10,000 gram/mole or greater. For ease of use, a poly(propylene glycol) that is a liquid at room temperature is often selected. Poly(propylene glycol) having a weight average molecular weight up to about 4000 g/mole or 5000 grams/mole tends to be a liquid at room temperature. Poly(propylene glycol) that is not a liquid at room temperature can be used if it is initially dissolved in a suitable organic solvent such as an alcohol (e.g., ethanol, n-propanol, or isopropanol). The weight average molecular weight of the poly(propylene glycol) is often in a range of 500 to 10,000 grams/mole, in a range of 1000 to 10,000 grams/mole, in a range of 1000 to 8000 grams/mole, in a range of 1000 to 5000 grams/mole, in a range of 1000 to 4000 grams/mole.

The second phase can contain up to 50 weight percent poly(propylene glycol). If higher amounts of the poly(propylene glycol) are used, there may be an insufficient amount of the monomer composition included in the second phase to form polymeric core particles that are uniformly shaped. In many embodiments, the second phase can contain up to 45 weight percent, up to 40 weight percent, up to 35 weight percent, up to 30 weight percent, or up to 25 weight percent poly(propylene glycol) based on a total weight of the second phase. The second phase typically contains at least 5 weight percent poly(propylene glycol). If lower amounts of the poly(propylene glycol) are used, the porosity of the resulting polymeric particles may be insufficient. That is, the void volume of the polymeric core particles may be insufficient to load and deliver an effective amount of a biologically active agent. The second phase typically can contain at least 10 weight percent, at least 15 weight percent, or at least 20 weight percent poly(propylene glycol). In some embodiments, the second phase contains 5 to 50 weight percent, 10 to 50 weight percent, 10 to 40 weight percent, 10 to 30 weight percent, 20 to 50 weight percent, 20 to 40 weight percent, or 25 to 35 weight percent poly(propylene glycol) based on the total weight of the second phase.

In some embodiments, the second phase contains 50 to 90 weight percent monomer composition and 10 to 50 weight percent poly(propylene glycol), 60 to 90 weight percent monomer composition and 10 to 40 weight percent poly(propylene glycol), 50 to 80 weight percent monomer composition and 20 to 50 weight percent poly(propylene glycol), or 60 to 80 weight percent monomer composition and 20 to 40 weight percent poly(propylene glycol) based on a total weight of the second phase.

In addition to the monomer composition and poly(propylene glycol), the second phase often contains an initiator for free radical polymerization of the monomer composition. Any suitable initiator known in the art can be used. The initiator can be a thermal initiator, a photoinitiator, or both. The specific initiator used is often selected based on its solubility in the second phase. The initiator is often used at a concentration of 0.1 to 5 weight percent, 0.1 to 3 weight percent, 0.1 to 2 weight percent, or 0.1 to 1 weight percent based on the weight of monomers in the monomer composition.

When a thermal initiator is added to the reaction mixture, polymeric particles can be formed at room temperature (i.e., 20 to 25 degrees Celsius) or at an elevated temperature. The temperature needed for polymerization often depends on the particular thermal initiator used. Examples of thermal initiators include organic peroxides and azo compounds.

When a photoinitiator is added to the reaction mixture, polymeric particles can be formed by the application of actinic radiation. Suitable actinic radiation includes electromagnetic radiation in the infrared region, visible region, ultraviolet region, or a combination thereof.

Examples of photoinitiators suitable in the ultraviolet region include, but are not limited to, benzoin, benzoin alkyl ethers (e.g., benzoin methyl ether and substituted benzoin alkyl ethers such anisoin methyl ether), phenones (e.g., substituted acetophenones such as 2,2-dimethoxy-2-phenylacetophenone and substituted alpha-ketols such as 2-methyl-2-hydroxypropiophenone), phosphine oxides, polymeric photoinitiators, and the like.

Commercially available photoinitiators include, but are not limited to, 2-hydroxy-2-methyl-1-phenyl-propane-1-one (e.g., commercially available under the trade designation DAROCUR 1173 from Ciba Specialty Chemicals), a mixture of 2,4,6-trimethylbenzoyl-diphenyl-phosphine oxide and 2-hydroxy-2-methyl-1-phenyl-propan-1-one (e.g., commercially available under the trade designation DAROCUR 4265 from Ciba Specialty Chemicals), 2,2-dimethoxy-1,2-diphenylethan-1-one (e.g., commercially available under the trade designation IRGACURE 651 from Ciba Specialty Chemicals), a mixture of bis(2,6-dimethoxybenzoyl)-2,4,4-trimethyl-pentylphosphine oxide and 1-hydroxy-cyclohexyl-phenyl-ketone (e.g., commercially available under the trade designation IRGACURE 1800 from Ciba Specialty Chemicals), a mixture of bis(2,6-dimethoxybenzoyl)-2,4,4-trimethyl-pentylphosphine oxide (e.g., commercially available under the trade designation IRGACURE 1700 from Ciba Specialty Chemicals), 2-methyl-1-[4-(methylthio)phenyl]-2-morpholinopropan-1-one (e.g., commercially available under the trade designation IRGACURE 907 from Ciba Specialty Chemicals), 1-hydroxy-cyclohexyl-phenyl-ketone (e.g., commercially available under the trade designation IRGACURE 184 from Ciba Specialty Chemicals), 2-benzyl-2-(dimethylamino)-1-[4-(4-morpholinyl)phenyl]-1-butanone (e.g., commercially available under the trade designation IRGACURE 369 from Ciba Specialty Chemicals), bis(2,4,6-trimethylbenzoyl)-phenylphosphine oxide (e.g., commercially available under the trade designation IRGACURE 819 from Ciba Specialty Chemicals), ethyl 2,4,6-trimethylbenzoyldiphenyl phosphinate (e.g., commercially available from BASF, Charlotte, N.C. under the trade designation LUCIRIN TPO-L), and 2,4,6-trimethylbenzoyldiphenylphosphine oxide (e.g., commercially available from BASF, Charlotte, N.C. under the trade designation LUCIRIN TPO).

The reaction mixture often includes at least 5 weight percent of the second phase (dispersed phase) and up to 95 weight percent of the first phase (continuous phase). In some embodiments, the reaction mixture contains 5 to 40 weight percent second phase and 60 to 95 weight percent first phase, 5 to 30 weight percent second phase and 70 to 95 weight percent first phase, 10 to 30 weight percent second phase and 70 to 90 weight percent first phase, or 5 to 20 weight percent second phase and 80 to 95 weight percent first phase. The weight percents are based on a total weight of the reaction mixture.

To prepare the polymeric core particles, droplets of the second phase are formed in the first phase. The components of the second phase are often mixed together prior to addition to the first phase. For example, the monomer composition, initiator, and the poly(propylene glycol) can be blended together and then this blended composition, which is the second phase, can be added to the first phase. The resulting reaction mixture is often mixed under high shear to form a micro-emulsion. The size of the dispersed second phase droplets can be controlled by the amount of shear, the mixing rate, and the composition. The size of the droplets can be determined by placing a sample of the mixture under an optical microscope prior to polymerization. Although any desired droplet size can be used, the average droplet diameter is often less than 200 micrometers, less than 100 micrometers, less than 50 micrometers, less than 25 micrometers, less than 10 micrometers, or less than 5 micrometers. For example, the average droplet diameter can be in the range of 1 to 200 micrometers, 1 to 100 micrometers, 5 to 100 micrometers, 5 to 50 micrometers, 5 to 25 micrometers, or 5 to 10 micrometers.

If a photoinitiator is used, the reaction mixture is often spread on a non-reactive surface to a thickness that can be penetrated by the desired actinic radiation. The reaction mixture is spread using methods that do not cause the droplets to coalesce. For example, the reaction mixture can be formed using an extrusion method. Often, the actinic radiation is in the ultraviolet region of the electromagnetic spectrum. If the ultraviolet radiation is applied from only the top surface of the reaction mixture layer, the thickness of the layer can be up to about 10 millimeters. If the reaction mixture layer is exposed to ultraviolet radiation from both the top and bottom surfaces, the thickness can be greater such as up to about 20 millimeters. The reaction mixture is subjected to the actinic radiation for a time sufficient to react the monomer composition and form polymeric particles. The reaction mixture layer is often polymerized within 5 minutes, within 10 minutes, within 20 minutes, within 30 minutes, within 45 minutes, or within 1 hour depending on the intensity of the actinic radiation source and the thickness of the reaction mixture layer.

If a thermal initiator is used, the droplets can be polymerized while continuing to mix the reaction mixture. Alternatively, the reaction mixture can be spread on a non-reactive surface to any desired thickness. The reaction mixture layer can be heated from the top surface, from the bottom surface, or both to form the polymeric core particles. The thickness is often selected to be comparable to that use with the use of actinic radiation such as ultraviolet radiation.

In many embodiments, a photoinitiator is preferred over a thermal initiator because lower temperatures can be used for polymerization. That is, the use of actinic radiation such as ultraviolet radiation can be used to minimize degradation of various components of the reaction mixture that might be sensitive to temperatures needed for use with thermal initiators. Further, the temperatures typically associated with the use of thermal initiators may undesirably alter the solubility of the various components of the reaction mixture between the first phase and the dispersed second phase.

During the polymerization reaction, the monomer composition reacts within the dispersed second phase droplets suspended in the first phase. As the polymerization progresses, the poly(propylene glycol) included in the second phase gets partially entrained within the polymerized product. Although it is possible that some portion of the poly(propylene glycol) can be covalently attached to the polymeric product through a chain transfer reaction, preferably the poly(propylene glycol) is not bonded to the polymeric product. The polymerized product is in the form of particles. In some embodiments, the particles are polymeric beads having a relatively uniform size and shape.

After formation of the polymerized product (i.e., polymeric particles containing entrained poly(propylene glycol)), the polymerized product can be separated from the first phase. Any suitable separation method can be used. For example, water is often added to lower the viscosity of the first phase. The particle of the polymerized product can be separated by decantation, filtration, or centrifugation. The particles of the polymerized product can be further washed by suspending them in water and collecting them a second time by decantation, filtration, centrifugation, or drying.

The particles of the polymerized product can then be subjected to one or more washing steps to remove the poly(propylene glycol) porogen. Suitable solvents for removing the poly(propylene glycol) include, for example, acetone, methyl ethyl ketone, toluene, and alcohols such as ethanol, n-propanol, or isopropanol. Stated differently, the entrained poly(propylene glycol) is removed from the polymerized product using solvent extraction methods. Pores are created where the poly(propylene glycol) previously resided.

In many embodiments, the resulting porous polymeric core particles (the polymerized product after removal of the poly(propylene glycol) porogen) have an average diameter that is less than 200 micrometers, less than 100 micrometers, less than 50 micrometers, less than 25 micrometers, less than 10 micrometers, or less than 5 micrometers. For example, the porous polymeric core particles can have an average diameter in the range of 1 to 200 micrometers, 1 to 100 micrometers, 5 to 100 micrometers, 5 to 50 micrometers, 5 to 25 micrometers, or 5 to 10 micrometers.

Figure 1B:
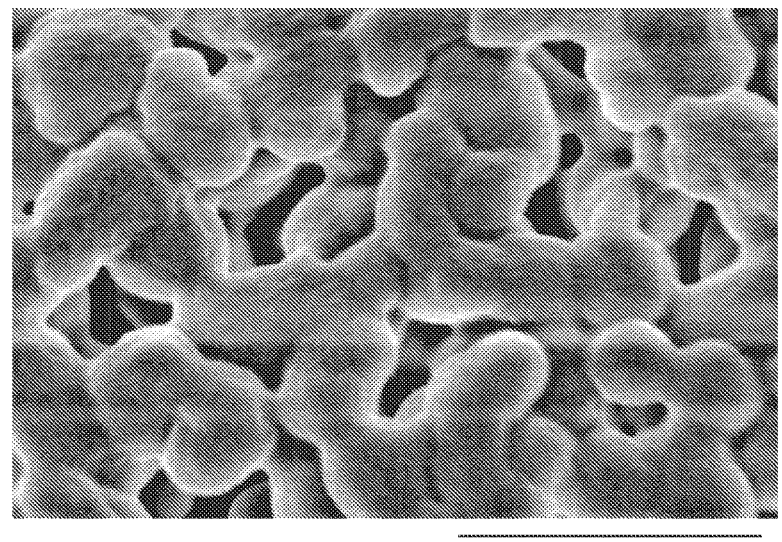
Figure 1C:
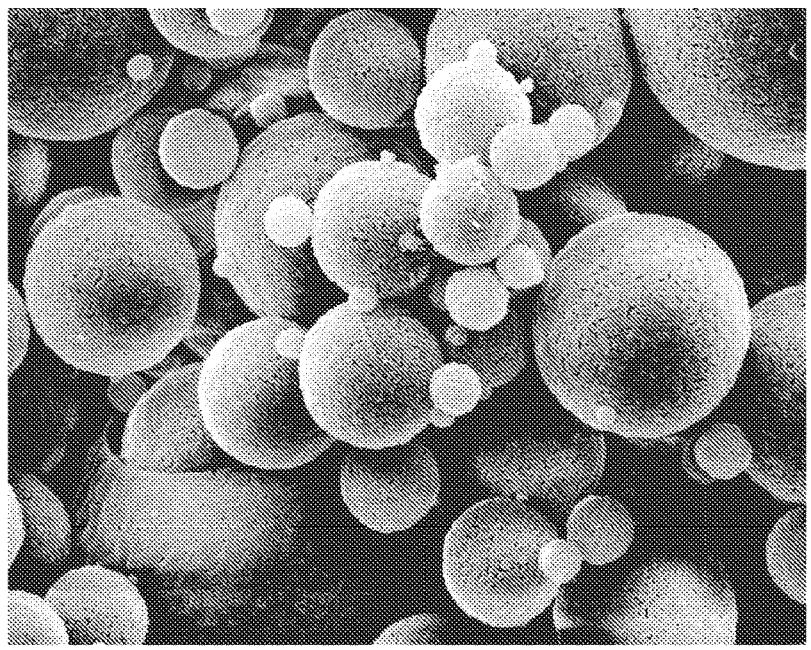

The polymeric core particles usually have multiple pores distributed over the surface of the particles as seen in FIGS. 1A, 1B, and 1C. Based on the diameter of the particles and the dimensions of the pores, the polymeric core particles can be described as being micro-particles (the average diameter is typically in a range of 1 to 200 micrometers, in the range of 1 to 100 micrometers, or in the range of 1 to 50 micrometers) and nano-porous (the pores have dimensions in an nanometer range such as in the range of 1 to 200 nanometers, in the range of 10 to 200 nanometers, in the range of 20 to 200 nanometers, or in the range of 50 to 200 nanometers). In some embodiments, the polymeric core particles are hollow in addition to having multiple pores distributed over the surface of the particles. As used herein, the term "hollow" refers to polymeric particles that have a polymeric exterior surrounding an inner region (cavity or core) that is not polymeric.

The porous polymeric core particles or the hollow and porous polymeric core particles are well suited for storage and delivery of a biologically active agent. That is, in certain embodiments, the porous polymeric core particles further include a biologically active agent. In particular, if all of the monomers in the monomer composition are hydrophobic, the polymeric core particles tend to be hydrophobic (i.e., hydrophobic polymeric core particles) and can accept (e.g., be loaded with) hydrophobic biologically active agents. If some of the monomers in the monomer composition are hydrophilic, however, the polymeric core particles tend to have sufficient hydrophilic character (i.e., hydrophilic polymeric core particles) to accept hydrophilic biologically active agents. Further, if the monomer composition includes a mixture of both hydrophobic monomers and hydrophilic monomers, the polymeric core particles tend to have sufficient hydrophobic and hydrophilic character to accept both hydrophobic and hydrophilic biologically active agents. In some embodiments, polymeric core particles having both hydrophobic and hydrophilic character can be desirable.

As used herein, the term "biologically active agent" refers to a compound that has some known effect on living systems such as, for example, a bacteria or other microorganism, plant, fish, insect, or mammal. The biologically active agent is added for the purpose of affecting the living system such as affecting the metabolism of the living system. Examples of biologically active agents include, but are not limited to, medicaments, herbicides, insecticides, antimicrobial agents, disinfectants and antiseptic agents, local anesthetics, astringents, antifungal agents (i.e., fungicides), antibacterial agents, growth factors, herbal extracts, antioxidants, steroids or other anti-inflammatory agents, compounds that promote wound healing, vasodilators, exfoliants, enzymes, proteins, carbohydrates, silver salts, and the like. Still other bioactive agents include artificial tanning agents, tanning accelerants, skin smoothing agents, skin tightening agents, anti-wrinkle agents, skin repair agents, anti-itch agents, hair growth agents, anti-acne agents, hair removal agents, corn removal agents, callus removal agents, wart removal agents, sunscreen agents, insect repellant agents, deodorants and antiperspirant agents, hair colorants or bleaching agents, and anti-dandruff agents. Any other suitable biologically active agent known in the art can be used. In some particular embodiments, the biologically active agents are agricultural chemicals such as, for example, herbicides, insecticides, and fungicides.

Any suitable method can be used to position (i.e., to load) the biologically active agent in the porous polymeric core particle once the porogen has been removed. The biologically active agent is typically positioned within the polymeric core particle prior to formation of the coating polymer layer around the polymeric core particle. In some embodiments, the biologically active agent is a liquid and the polymeric core particles are mixed with the liquid to load the biologically active agent (e.g., to position the biologically active agent within the polymeric core particles). In other embodiments, the biologically active agent can be dissolved in a suitable organic solvent or water and the polymeric core particles are exposed to the resulting solution. Any organic solvent that is used is typically selected so that it does not dissolve the polymeric core particles. When an organic solvent or water is used, at least some of the organic solvent or water may be loaded within the polymeric core particle in addition to the biologically active agent.

When the biologically active agent is dissolved in an organic solvent or water, the concentration is typically selected to be as great as possible to shorten the time needed to load a suitable amount of the biologically active agent within the polymeric core particle. The amount of biologically active agent loaded and the amount of time required for loading (i.e., positioning within the polymeric core particle) are often dependent, for example, on the composition of the monomers used to form the polymeric core particle, the rigidity of the polymeric core particle (e.g., the amount of crosslinking), and the compatibility of the biologically active agent with the polymeric core particle. The loading time is often less than 24 hours, less than 18 hours, less than 12 hours, less than 8 hours, less than 4 hours, less than 2 hours, less than 1 hour, less than 30 minutes, less than 15 minutes, or less than 5 minutes. After loading, the particles are typically separated from the solution containing the biologically active agent by decantation, filtration, centrifugation, or drying.

The volume of biologically active agent loaded can be up to the volume of poly(propylene glycol) removed from the polymerized product used to form the polymeric core particles. That is, the biologically active agent can fill the voids left after removal of the poly(propylene glycol). In many embodiments, the amount of biologically active agent loaded can be up to 50 weight percent based on a total weight of the polymeric core particle after loading (i.e., polymeric core particles plus the loaded biologically active agent). In some example loaded polymeric core particles loaded, the amount of the biologically active agent can be up to 40 weight percent, up to 30 weight percent, 25 weight percent, up to 20 weight percent, up to 15 weight percent, up to 10 weight percent, or up to 5 weight percent. The amount of biologically active agent is typically at least 0.1 weight percent, at least 0.2 weight percent, at least 0.5 weight percent, at least 1 weight percent, at least 5 weight percent, or at least 10 weight percent. Some loaded polymeric core particles contain 0.1 to 50 weight percent, 0.5 to 50 weight percent, 1 to 50 weight percent, 5 to 50 weight percent, 1 to 40 weight percent, 5 to 40 weight percent, 10 to 40 weight percent, or 20 to 40 weight percent biologically active agent. Because the porous polymeric core particles tend to be highly crosslinked, they tend to swell little even after loading of the biologically active agent. That is, the average sizes of the porous polymeric core particles are comparable before and after loading of the biologically active agent.

To be released from the loaded polymeric core particles, the biologically active agent typically diffuses through a coating layer positioned around the polymeric core particle. Diffusion may occur, for example, through an opening within the polymeric matrix of the coating layer, through defects in the coating layer, or by any other mechanism. The thickness and composition of the coating layer as well as the environment surrounding the polymeric composite particle can affect the rate of diffusion of the biologically active material out of the porous polymeric core and through the coating layer.

Depending on the environment and other factors, the release may or may not occur immediately. That is, the onset of release of the biologically active agent may commence immediately or after a certain period of time. Once release commences, however, the amount of the biologically active agent released is usually greatest initially and then decreases over time. Such a release profile can arise when the biologically active agent is more concentrated at the outer edge of the loaded porous polymeric core particle. Such a release profile can also arise when the biologically active agent is distributed uniformly throughout the core polymeric particle because additional time is needed to diffuse from the inner regions of the polymeric core particle.

The coating layer around the polymeric core particle, which in most instances is a loaded polymeric core particle, contains a thermoplastic polymer, a wax, or a mixture thereof. Any suitable thermoplastic polymer and/or wax can be used that allows release of the biologically active agent from the porous polymeric core particle though the coating layer. The thermoplastic polymeric material and/or wax are typically selected to be soluble or dispersible in water, an organic solvent, or a mixture thereof. Neither the thermoplastic polymeric material nor the wax is tacky (i.e., the glass transition temperature is typically at least 20° C.). The thermoplastic polymer is typically selected to be rubbery and not brittle. The thermoplastic polymer is typically a linear polymer and is not crosslinked or crosslinked to such a low amount that it can still be dissolved or dispersed in water, an organic solvent, or a mixture thereof.

The coating layer can be formed by deposition from a coating solution containing the thermoplastic polymer and/or wax. That is, the thermoplastic polymer and/or wax is dissolved in a suitable liquid medium. If the biologically active agent is a non-polar compound (e.g., hydrophobic compound), it is often preferable to use a polar liquid such as water, a polar organic solvent, or a mixture thereof to prepare the coating solution used to form the coating layer; the thermoplastic polymer and/or wax is selected to be soluble in the polar liquid. Conversely, if the biologically active agent is a polar compound (e.g., a hydrophilic compound), it is often preferable to use a non-polar liquid such as a non-polar organic solvent to prepare the coating solution; the thermoplastic polymer can be selected to be soluble in the non-polar organic solvent.

Alternatively, the coating layer can be formed by deposition from a coating dispersion containing the thermoplastic polymer and/or wax. In many embodiments, the thermoplastic polymer and/or wax is dispersed in water. Such water-based dispersions can be used with polar or non-polar biologically active agents. That is, if the dispersions have a sufficiently high weight percent solids content (e.g., greater than 10 weight percent, greater than 20 weight percent, or greater than 25 weight percent, or greater than 30 weight percent), extraction of the biologically active agent from the porous core particle can be minimized regardless of the polarity of the biologically active agent.

The composition of the coating solution or coating dispersion is selected so that a significant amount of the biologically active agent is not extracted out of the loaded polymeric core particle during the deposition of the thermoplastic polymer and/or wax. In some embodiments, the coating solution or coating dispersion extracts less than 10 weight percent, less than 5 weight percent, less than 3 weight percent, less than 2 weight percent, or less than 1 weight percent of the biologically active agent from the loaded polymeric core particle.

In some embodiments, the biologically active agent is a polar compound and the coating solution contains a non-polar organic solvent such as, for example, an alkane (e.g., pentane, hexane, or cyclohexane), benzene, toluene, ketone (e.g., acetone, methyl ethyl ketone, or methyl isobutyl ketone), ether (e.g., diethyl ether or 1,4-dioxane), chloroform, dichloromethane, or the like. The amount of thermoplastic polymer and/or wax in the coating solution depends on its solubility in the non-polar organic solvent, the desired viscosity of the solution, and the desired thickness of the coating layer. In many embodiments, the thermoplastic polymer and/or wax is present in an amount equal to at least 5 weight percent, at least 10 weight percent, or at least 10 weight percent and up to 50 weight percent, up to 40 weight percent, up to 30 weight percent, or up to 20 weight percent based on a total weight of the coating solution.

Suitable thermoplastic polymers for use in the coating solution when the biologically active agent is a polar compound include, but are not limited to, silicone-based thermoplastic polymers, (meth)acrylate-based thermoplastic polymers, olefin-based thermoplastic polymers, and styrene-based thermoplastic polymers.

Suitable silicone-based thermoplastic polymers include those having at least one polydiorganosiloxane unit of formula $(\text{—Si}(R^7)_2\text{O—})_a$ where a is an integer equal to at least 3 and $R^7$ is an alkyl, haloalkyl, alkenyl, aralkyl, aryl, or aryl substituted with an alkyl, alkoxy, or halo. The silicone-based thermoplastic polymers are often a urea-based silicone copolymer, an oxamide-based silicone copolymer, an amide-based silicone copolymer, a urethane-based silicone copolymer, or mixtures thereof. As used herein, the term "urea-based" refers to a segmented copolymer having at least one urea linkage, the term "oxamide-based" refers to a segmented copolymer having at least one oxamide linkage, the term "amide-based" refers to a segmented copolymer having at least one amide linkage, the term "urethane-based" refers to a segmented copolymer having at least one urethane linkage.

These silicone-based thermoplastic polymers are often prepared from a polydiorganosiloxane diamines represented by Formula (VIII).

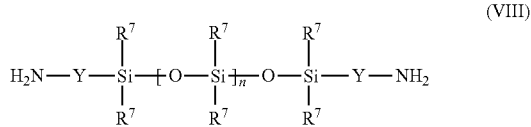

(VIII)

In Formula (VIII), each $R^7$ is independently an alkyl, haloalkyl, alkenyl, aralkyl, aryl, or aryl substituted with an alkyl, alkoxy, or halo. Each Y is independently an alkylene, arylene, or aralkylene as defined above for Formula (I). The variable n is an integer of 0 to 1500. For example, subscript n can be an integer up to 1000, up to 500, up to 400, up to 300, up to 200, up to 100, up to 80, or up to 60. The value of n is often at least 40, at least 45, at least 50, or at least 55. For example, subscript n can be in the range of 40 to 1500, 40 to 1000, 40 to 500, 50 to 500, 50 to 400, 50 to 300, 50 to 200, 50 to 100, 50 to 80, or 50 to 60.

Suitable alkyl groups for $R^7$ in Formula (VIII) typically have 1 to 10 carbon atoms, 1 to 6 carbon atoms, or 1 to 4 carbon atoms. Exemplary alkyl groups include, but are not limited to, methyl, ethyl, isopropyl, n-propyl, n-butyl, and iso-butyl. Suitable haloalkyl groups for $R^7$ often have only a portion of the hydrogen atoms of the corresponding alkyl group replaced with a halogen. Exemplary haloalkyl groups include chloroalkyl and fluoroalkyl groups with 1 to 3 halo atoms and 3 to 10 carbon atoms. Suitable alkenyl groups for $R^7$ often have 2 to 10 carbon atoms. Exemplary alkenyl groups often have 2 to 8, 2 to 6, or 2 to 4 carbon atoms. Suitable aryl groups for $R^7$ often have 6 to 12 carbon atoms. Phenyl is an exemplary aryl group. The aryl group can be unsubstituted or substituted with an alkyl (e.g., an alkyl having 1 to 10 carbon atoms, 1 to 6 carbon atoms, or 1 to 4 carbon atoms), an alkoxy (e.g., an alkoxy having 1 to 10 carbon atoms, 1 to 6 carbon atoms, or 1 to 4 carbon atoms), or halo (e.g., chloro, bromo, or fluoro). Suitable aralkyl groups for $R^7$ often have an alkyl group having 1 to 10 carbon atoms that is substituted with an aryl group having 6 to 12 carbon atoms. Exemplary aralkyl groups include an alkyl group having 1 to 10 carbon atoms, 1 to 6 carbon atoms, or 1 to 4 carbon atoms that is substituted with a phenyl group.

In many embodiments, at least 50 percent of the $R^7$ groups are methyl. For example, at least 60 percent, at least 70 percent, at least 80 percent, at least 90 percent, at least 95 percent, at least 98 percent, or at least 99 percent of the $R^7$ groups can be methyl. The remaining $R^6$ groups can be selected from an alkyl having at least two carbon atoms, haloalkyl, aralkyl, alkenyl, aryl, or aryl substituted with an alkyl, alkoxy, or halo. For example, all the $R^7$ groups can be an alkyl (e.g., methyl or ethyl) or an aryl (e.g., phenyl).

Each Y in Formula (VIII) is independently an alkylene, an aralkylene, an arylene, or a combination thereof. Exemplary alkylenes, which can be linear or branched and often have 1 to 10 carbon atoms, 1 to 6 carbon atoms, or 1 to 4 carbon atoms. Exemplary arylenes often have 6 to 20 carbon atoms, 6 to 12 carbon atoms, or 6 carbon atoms (i.e., phenylene). Exemplary aralkylenes often have 7 to 20 carbon atoms, 7 to 18 carbon atoms, 7 to 12 carbon atoms. Aralkylene often include a phenylene group attached to an alkylene having 1 to 12 carbon atoms, 1 to 10 carbon atoms, or 1 to 6 carbon atoms. In many embodiments, Y is an alkylene group.

Specific examples of polydiorganosiloxane diamines include, but are not limited to, polydimethylsiloxane diamine, polydiphenylsiloxane diamine, polytrifluoropropylmethylsiloxane diamine, polyphenylmethylsiloxane diamine, polydiethylsiloxane diamine, polydivinylsiloxane diamine, polyvinylmethylsiloxane diamine, poly(5-hexenyl) methylsiloxane diamine, and mixtures thereof.

The polydiorganosiloxane diamine of Formula (VIII) can be prepared by any known method and can have any suitable molecular weight, such as a weight average molecular weight in the range of 700 to 150,000 grams per mole (Daltons), in the range of 1,000 to 100,000 grams per mole, in the range of 5,000 to 50,000 grams per mole, or in the range of 10,000 to 40,000 grams per mole, or in the range of 20,000 to 30,000 grams per mole.

Suitable polydiorganosiloxane diamines and methods of making the polydiorganosiloxane diamines are described, for example, in U.S. Pat. No. 3,890,269 (Martin), U.S. Pat. No. 4,661,577 (Lane et al.), U.S. Pat. No. 5,026,890 (Webb et al.), U.S. Pat. No. 5,276,122 (Aoki et al.), U.S. Pat. No. 5,214,119 (Leir et al.), U.S. Pat. No. 5,461,134 (Leir et al.), U.S. Pat. No. 5,512,650 (Leir et al.), and U.S. Pat. No. 6,355,759 (Sherman et al.). Some polydiorganosiloxane diamines are commercially available, for example, from Shin Etsu Silicones of America, Inc. (Torrance, Calif., USA) and from Gelest Inc. (Morrisville, Pa., USA).

A first example of a useful silicone-based silicone polymer is a silicone polyurea block copolymer. Silicone polyurea block copolymers are the reaction product of a polydiorganosiloxane diamine (also referred to as a silicone diamine) of Formula (VIII), a polyisocyanate, and an optional organic polyamine. As used herein, the term "polyisocyanate" refers to a compound having more than one isocyanate group. As used herein, the term "polyamine" refers to a compound having more than one amino group (e.g., primary amino group, secondary amino group, or combination thereof). The term "organic polyamine" refers to a polyamine that does not include a silicone group (i.e., the polyamine is not of Formula (VIII)).

Any polyisocyanate that can react with the above-described polydiorganosiloxane diamine can be used. The polyisocyanates are typically diisocyanates but small amounts of triisocyanates can be included. Examples of suitable diisocyanates include aromatic diisocyanates such as 2,6-toluene diisocyanate, 2,5-toluene diisocyanate, 2,4-toluene diisocyanate, m-phenylene diisocyanate, p-phenylene diisocyanate, methylenediphenylene-4,4'-diisocyanate, polycarbodiimide-modified methylenediphenylene diisocyanate, (4,4'-diisocyanato-3,3',5,5'-tetraethyl) diphenylmethane, 4,4-diisocyanato-3,3'-dimethoxybiphenyl (o-dianisidine diisocyanate), 5-chloro-2,4-toluene diisocyanate, 1-chloromethyl-2,4-diisocyanato benzene, m-xylylene diisocyanate and tetramethyl-m-xylylene diisocyanate; and aliphatic diisocyanates such as 1,4-diisocyanatobutane, 1,6-diisocyanatohexane, 1,12-diisocyanatododecane, and 2-methyl-1,5-diisocyanatopentane; and cycloaliphatic diisocyanates such as methylenedicyclohexylene-4,4'-diisocyanate, 3-isocyanatomethyl-3,5,5-trimethylcyclohexyl isocyanate (isophorone diisocyanate), and cyclohexylene-1,4-diisocyanate. Examples of suitable triisocyanates include those produced from biurets, isocyanurates, and adducts. Examples of commercially available polyisocyanates include portions of the series of polyisocyanates available under the trade designations DESMODUR and MONDUR from Bayer and PAPI from Dow Plastics (Midland, Mich., USA).

Examples of useful optional organic polyamines include polyoxyalkylene diamines such as those commercially available under the trade designation D-230, D-400, D-2000, D-4000, ED-2001 and EDR-148 from Hunstman Corporation (Houston, Tex., USA), polyoxyalkylene triamines such as those commercially available under the trade designations T-403, T-3000 and T-5000 from Hunstman Corporation, alkylene diamines such as ethylene diamine, and various polyamines commercially available from INVISTA Specialty Intermediates (Wilmington, Del., USA) under the trade designation DYTEK (e.g., DYTEK A is 2-methylpentamethylenediamine and DYTEK EP is 1,3-pentanediamine).

The silicone polyurea block copolymers can be represented by the repeating unit of Formula (IX) with a urea linkage of formula —NH—(CO)-ND-.

nylene, or heteroalkylene. Examples of heteroalkylenes include divalent radicals of polyethylene oxide (also called poly(oxyethylene)), polypropylene oxide (also called poly (oxypropylene)), polytetramethylene oxide (also called poly (oxytetramethylene)), and copolymers and mixtures thereof.

The variable p is a number that is at least 1 such as 1 to 10, 1 to 5, or 1 to 3. Each asterisk (*) indicates a site of attachment of the repeat unit to another group in the copolymer such as, for example, another repeat unit of Formula (IX).

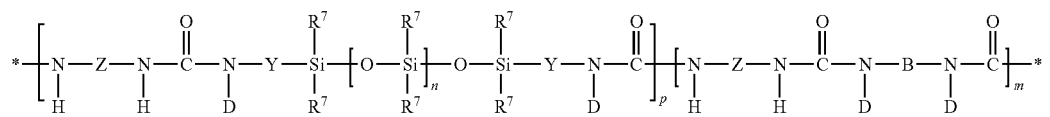

(IX)

The groups $R^7$ and Y as well as the variable n are the same as defined above for the polydiorganosiloxane of Formula (VIII). Each D is selected from hydrogen, an alkyl (e.g., an alkyl having 1 to 10 carbon atoms, 1 to 6 carbon atoms, or 1 to 4 carbon atoms), an aryl having 6 to 12 carbon atoms (e.g., phenyl), or a radical that completes a ring structure including B or Y to form a heterocycle. Each D is often hydrogen or an alkyl group.

Each group Z in Formula (IX) is equal to the polyisocyanate minus the multiple isocyanate groups (e.g., minus the two isocyanate groups). In many embodiments, each Z is independently an arylene, aralkylene, or alkylene. Exemplary arylenes have 6 to 20 carbon atoms and exemplary aralkylenes have 7 to 20 carbon atoms. The arylenes and aralkylenes can be unsubstituted or substituted with an alkyl (e.g., an alkyl having 1 to 10 carbon atoms, 1 to 6 carbon atoms, or 1 to 4 carbon atoms), an alkoxy (e.g., an alkoxy having 1 to 10 carbon atoms, 1 to 6 carbon atoms, or 1 to 4 carbon atoms), or halo (e.g., chloro, bromo, or fluoro). The alkylenes can be linear branch, cyclic, or combinations thereof and can have 1 to 20 carbon atoms. In some embodiments Z is 2,6-tolylene, 4,4'-methylenediphenylene, 3,3'-dimethoxy-4,4'-biphenylene, tetramethyl-m-xylylene, 4,4'-methylenedicyclohexylene, 3,5,5-trimethyl-3-methylenecyclohexylene, 1,6-hexamethylene, 1,4-cyclohexylene, 2,2,4-trimethylhexylene, and mixtures thereof.

In no optional organic polyamine is used, the variable m in Formula (IX) is equal to zero. If an organic polyamine is used, the variable m in Formula (I) has a value greater than zero. For example, m is in a range of 0 to 1000, in a range of 0 to 500, in a range of 0 to 200, in a range of 0 to 100, in a range of 0 to 50, in a range of 0 to 20, or in a range of 0 to 10.

The group B in Formula (I) is equal to the polyamine minus the multiple amine groups (e.g., minus two amine groups). Group B is often selected from an alkylene (e.g., an alkylene having 1 to 10 carbon atoms, 1 to 6 carbon atoms, or 1 to 4 carbon atoms), aralkylene, arylene such as phe- Useful silicone polyurea block copolymers are disclosed in, e.g., U.S. Pat. No. 5,512,650 (Leir et al.), U.S. Pat. No. 5,214,119 (Leir et al.), U.S. Pat. No. 5,461,134 (Leir et al.), U.S. Pat. No. 6,407,195 (Sherman et al.), U.S. Pat. No. 6,441,118 (Sherman et al.), U.S. Pat. No. 6,846,893 (Sherman et al.), and U.S. Pat. No. 7,153,924 (Kuepfer et al.) as well as in PCT Publication No. WO 97/40103 (Paulick et al.).

A second example of a useful silicone-based silicone polymer is a polydiorganosiloxane polyoxamide block copolymer. The polydiorganosiloxane polyoxamide block copolymers are typically the reaction product of a silicone diamine such as that shown in Formula (VIII), an oxalate compound, and an organic polyamine (e.g., an organic diamine). Examples of polydiorganosiloxane polyoxamide block copolymers are described, for example, in US Patent Application Publication No. 2007/0148474 (Leir et al.). The polydiorganosiloxane polyoxamide block copolymer contains at least two repeat units of Formula (X).

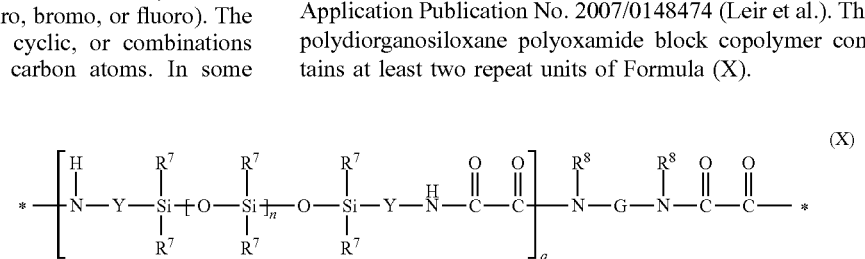

(X)

In Formula (X), group Y, group $R^7$, and variable n are the same as described above for Formula (VIII). That is, each $R^7$ is independently an alkyl, haloalkyl, aralkyl, alkenyl, aryl, or aryl substituted with an alkyl, alkoxy, or halo. Each asterisk (*) indicates a site of attachment of the repeat unit to another group in the copolymer such as, for example, another repeat unit of Formula (III).

The subscript q is an integer of 1 to 10. For example, the value of q is often an integer up to 9, up to 8, up to 7, up to 6, up to 5, up to 4, up to 3, or up to 2. The value of q can be in the range of 1 to 8, 1 to 6, or 1 to 4.

Group G in Formula (X) is a residual unit that is equal to a diamine compound of formula $R^8HN$-G-$NHR^8$ minus the two amino groups (i.e., —$NHR^8$ groups). Group $R^8$ is hydrogen or alkyl (e.g., an alkyl having 1 to 10, 1 to 6, or 1 to 4 carbon atoms) or $R^8$ taken together with G and with the nitrogen to which they are both attached forms a heterocyclic group (e.g., $R^8$HN-G-NHR$^8$ is piperazine or the like). The diamine can have primary or secondary amino groups. In most embodiments, $R^8$ is hydrogen or an alkyl. In many embodiments, both of the amino groups of the diamine are primary amino groups (i.e., both $R^8$ groups are hydrogen) and the diamine is of formula $H_2$N-G-NH$_2$.

In some embodiments, G is an alkylene, heteroalkylene, polydiorganosiloxane, arylene, aralkylene, or a combination thereof. Suitable alkylenes often have 2 to 10, 2 to 6, or 2 to 4 carbon atoms. Exemplary alkylene groups include ethylene, propylene, butylene, and the like. Suitable heteroalkylenes are often polyoxyalkylenes such as polyoxyethylene having at least 2 ethylene units, polyoxypropylene having at least 2 propylene units, or copolymers thereof. Suitable polydiorganosiloxanes include the polydiorganosiloxane diamines of Formula (VIII), which are described above, minus the two amino groups. Exemplary polydiorganosiloxanes include, but are not limited to, polydimethylsiloxanes with alkylene Y groups. Suitable aralkylene groups usually contain an arylene group having 6 to 12 carbon atoms bonded to an alkylene group having 1 to 10 carbon atoms. Some exemplary aralkylene groups are phenylene-alkylene where the phenylene is bonded to an alkylene having 1 to 10 carbon atoms, 1 to 8 carbon atoms, 1 to 6 carbon atoms, or 1 to 4 carbon atoms. As used herein with reference to group G, "a combination thereof" refers to a combination of two or more groups selected from an alkylene, heteroalkylene, polydiorganosiloxane, arylene, and aralkylene. A combination can be, for example, an aralkylene bonded to an alkylene (e.g., alkylene-arylene-alkylene). In one exemplary alkylene-arylene-alkylene combination, the arylene is phenylene and each alkylene has 1 to 10, 1 to 6, or 1 to 4 carbon atoms.

The polydiorganosiloxane polyoxamide tends to be free of groups having a formula —R$^a$—(CO)—NH— where R$^a$ is an alkylene. All of the carbonylamino groups along the backbone of the copolymeric material are part of an oxalylamino group (i.e., the —(CO)—(CO)—NH— group). That is, any carbonyl group along the backbone of the copolymeric material is bonded to another carbonyl group and is part of an oxalyl group. More specifically, the polydiorganosiloxane polyoxamide has a plurality of aminoxalylamino groups.

A third example of useful silicone-based silicone polymers are amide-based silicone copolymers. Such polymers are similar to the urea-based polymers, containing amide linkages (—N(D)-(CO)— with the carbonyl group bonded to an alkylene or arylene group) instead of urea linkages (—N(D)-(CO)—NH—). Group D is the same as defined above for Formula (IX) and is often hydrogen or alkyl.

The amide-based silicone copolymers may be prepared in a variety of different ways. Starting from the polydiorganosiloxane diamine described above in Formula (VIII), the amide-based copolymer can be prepared by reaction with a poly(carboxylic acid) or a poly(carboxylic acid) derivative such as, for example, esters of the poly(carboxylic acid). In some embodiments, the amide-based silicone elastomer is prepared by the reaction of a polydiorganosiloxane diamine and dimethyl salicylate of adipic acid.

An alternative reaction pathway to amide-based silicone elastomers utilizes a silicone di-carboxylic acid derivative such as a carboxylic acid ester. Silicone carboxylic acid esters can be prepared through the hydrosilation reaction of a silicone hydride (i.e. a silicone terminated with a silicon-hydride (Si—H) group) and an ethylenically unsaturated ester. For example a silicone di-hydride can be reacted with an ethylenically unsaturated ester such as, for example, $CH_2$=CH—$(CH_2)_v$—(CO)—OR, where —(CO)- represents a carbonyl group and v is an integer up to 15, and R is an alkyl, aryl or substituted aryl group, to yield a silicone chain capped with —Si—$(CH_2)_{v+2}$—(CO)—OR. The —(CO)—OR group is a carboxylic acid derivative which can be reacted with a silicone diamine, a polyamine or a combination thereof. Suitable silicone diamines and polyamines have been discussed above and include aliphatic, aromatic or oligomeric diamines (such as ethylene diamine, phenylene diamine, xylylene diamine, polyoxalkylene diamines, etc).

Another useful class of silicone elastomers is urethane-based silicone polymers such as silicone polyurea-urethane block copolymers. Silicone polyurea-urethane block copolymers include the reaction product of a polydiorganosiloxane diamine (also referred to as silicone diamine), a diisocyanate, and an organic polyol. Such materials are structurally very similar to the structure of Formula (IX) except that the —N(D)-B—N(D)-links are replaced by —O—B—O-links. Examples are such polymers are further described in U.S. Pat. No. 5,214,119 (Leir et al.). These urethane-based silicone polymers are prepared in the same manner as the urea-based silicone polymers except that an organic polyol is substituted for the organic polyamine. Typically, since the reaction between an alcohol and an isocyanate is slower than the reaction between an amine and an isocyanate, a catalyst is used. The catalyst is often a tin-containing compound.

Another class of thermoplastic polymers for use in coating solutions where the biologically active agent is polar (e.g., hydrophilic) are (meth)acrylate-based polymers. In many embodiments, the monomers used to form the (meth)acrylate-based polymers are alkyl (meth)acrylates. For example, at least 90 weight percent, at least 95 weight percent, at least 98 weight percent, at least 99 weight percent, or 100 weight percent of the monomers are alkyl (meth)acrylates. These polymers can be dissolved in organic solvents such as, for example, toluene, benzene, alkanes (e.g., pentane, cyclohexane, or hexane), and chlorinated solvents such as chloroform and dichloromethane.

The alkyl (meth)acrylates are typically those having an alkyl group with 1 to 20 carbon atoms. The alkyl group can be linear, branched, cyclic, or a combination thereof. Suitable examples include, but are not limited to, methyl (meth)acrylate, ethyl (meth)acrylate, n-propyl (meth)acrylate, isopropyl (meth)acrylate, n-butyl (meth)acrylate, isobutyl (meth)acrylate, tert-butyl (meth)acrylate, n-pentyl (meth)acrylate, isopentyl (meth)acrylate, 2-methylbutyl (meth)acrylate, n-hexyl (meth)acrylate, cyclohexyl (meth)acrylate, 4-methyl-2-pentyl (meth)acrylate, 2-methylhexyl (meth)acrylate, 3,3,5-trimethylcyclohexyl (meth)acrylate, isobornyl (meth)acrylate, 2-ethylhexyl (meth)acrylate, n-octyl (meth)acrylate, isooctyl (meth)acrylate, 2-octyl (meth)acrylate, isononyl (meth)acrylate, isoamyl (meth)acrylate, n-decyl (meth)acrylate, isodecyl (meth)acrylate, 2-propylheptyl (meth)acrylate, isotridecyl (meth)acrylate, isostearyl (meth)acrylate, octadecyl (meth)acrylate, 2-octyldecyl (meth)acrylate, dodecyl (meth)acrylate, lauryl (meth)acrylate, and heptadecanyl (meth)acrylate. In many embodiments, the alkyl (meth)acrylate is an alkyl methacrylate.

The alkyl methacrylates tend to have a higher glass transition temperature than alkyl acrylates and so may be more suitable for use in preparation of the (meth)acrylate-based polymer. However, some alkyl acrylates can be included in the (meth)acrylate as long as the glass transition temperature is at least 20° C., at least 40° C., at least 50° C., at least 60° C., at least 80° C., or at least 100° C. Specific examples of (meth)acrylate polymers include various homopolymers such as, for example, poly(methyl methacrylate), poly(ethyl methacrylate), and polybutyl methacrylate as well as various copolymers such as, for example, poly(butyl methacrylate)-co-poly(isobutyl methacrylate) and the like. Such polymers can be obtained, for example, from Polysciences, Inc. (Warrington, Pa., USA).

Any suitable molecular weight can be used for the (meth)acrylate-based polymer. The molecular weight should be high enough to form a film but not so high that the (meth)acrylate-based polymer is difficult to dissolve in an organic solvent or that the resulting solution has a viscosity that is too high for deposition on the porous core polymeric particles. The weight average molecular weight is often at least 1,000 Daltons (grams/mole), at least 2,000 Daltons, at least 5,000 Daltons, at least 10,000 Daltons, or at least 20,000 Daltons. The weight average molecular weight can be, for example, up to 500,000 Daltons or higher, up to 400,000 Daltons, up to 200,000 Daltons, or up to 100,000 Daltons.

In other embodiments where the loaded biologically active agent is a polar compound, the coating solution can contain a wax dissolved in an organic solvent such as toluene, benzene, an alkane, an alcohol, or the like. The wax can be a naturally occurring or synthetic material. Example waxes include, but are not limited to, animal waxes such as beeswax and lanolin, vegetable waxes such as Carnauba wax, petroleum waxes such as paraffin, and hydrogenated oils such as hydrogenated vegetable oils. Example hydrogenated oils include hydrogenated castor oil such as that commercially available under the trade designation CASTORWAX from Vertellus (Indianapolis, Ind., USA)). Still other waxes low density polyethylene such as those, for example, of formula $CH_3-(CH_2)_m-CH_3$ where m is in a range of about 50 to 100.

In still other embodiments, the biologically active agent is a non-polar compound (e.g., hydrophobic compound) and the coating solution contains a thermoplastic polymer dissolved in water or a polar organic solvent such as, for example, an alcohol (e.g., methanol, ethanol, n-propanol, isopropanol, n-butanol, and the like), tetrahydrofuran, acetonitrile, dimethylformamide, dimenthylsulfoxide, dichloromethane, propylene carbonate, acetone, methyl ethyl ketone, methyl isobutyl ketone, or the like. In many embodiments, the coating solution contains water and/or an alcohol. The amount of thermoplastic polymer in the solution depends on the desired viscosity of the solution and the solubility of the thermoplastic polymer in water and/or polar organic solvent. In many embodiments, the thermoplastic polymer is present in an amount equal to at least 5 weight percent, at least 10 weight percent, or at least 15 weight percent and up to 50 weight percent, up to 40 weight percent, up to 30 weight percent, or up to 20 weight percent based on a total weight of the thermoplastic polymer solution.

Suitable thermoplastic polymers include, but are not limited to, poly(N-vinyl pyrrolidone), (meth)acrylate-based polymers with acidic groups (such as copolymers of an alkyl (meth)acrylate as described above and (meth)acrylic acid), polyesters, polyamides, and polyvinyl alcohols. The weight average molecular weight is often at least 1,000 Daltons, at least 2,000 Daltons, at least 5,000 Daltons, or at least 10,000 Daltons. The weight average molecular weight can be up to 500,000 Daltons or higher. For example, the weight average molecular weight can be up to 300,000 Daltons, up to 200,000 Daltons, up to 100,000 Daltons, up to 50,000 Daltons, up to 20,000 Daltons. Some such thermoplastic polymers can be obtained, for example, from Polysciences, Inc. (Warrington, Pa., USA).

In still other embodiments, a coating dispersion is used to form the coating layer. The coating dispersion is often a water-based dispersion of a wax and/or thermoplastic polymer. An example water-based dispersion of a thermoplastic polymer contains phenoxy resin (polyhydroxy ethers) such as those formed from epichlorohydrin and Bisphenol A. Such water-based dispersions are commercially available from InChemRex under the trade designation PKHW (e.g., PKHW 34, PKHW 35, and PKHW 38). Wax dispersions typically contain a wax having a hydrophilic group that allows dispersion in water. Examples include dispersions of polyethylene, paraffin waxes, carnauba wax, and the like. Such materials are commercially available under the trade designation SYNCERA from Paramelt (Muskegon, Mich., USA), under the trade designation LIQUITRON from Lubrizol Advanced Materials, Inc. (McCook, Ill., USA), and under the trade designation CARNAUBA MILK from Koster Keunen (Watertown, Conn., USA). These dispersions often have percent solids in the range of 10 to 60 weight percent, 20 to 50 weight percent, or 30 to 40 weight percent. The high percent solids content of the water-based dispersions tends to disfavor extraction of the biologically active agent from the porous polymeric core, even when the biologically active agent is soluble in water.

Any suitable method can be used to deposit the coating around the polymeric core particle. In most embodiments, the porous polymeric core particles contains loaded biologically active agent at the time the coating layer is deposited. That is, the coating layer is formed around loaded polymeric core particles. The coating solution or coating dispersion is mixed with the porous polymeric core particles (e.g., loaded polymeric core particles). After sufficient mixing, the solvent is removed to provide a coating layer. The resulting particles are polymeric composite particles if the polymeric core particles were loaded with a biologically active agent.

For many embodiments of the polymeric composite particles, the coating layer surrounds the porous polymeric core particle as a shell layer. Stated differently, the polymeric composite particles are core-shell polymeric particles. Prior to release of the biologically active agent, the porous polymeric composite particles have a core-shell structure with the porous polymeric core particles containing loaded biologically active agent. In some embodiments, the shell layer (coating layer) surrounds a single porous polymeric core particle. That is, the porous polymeric composite particle contains a single porous polymeric core particle. In other embodiments, however, the shell surrounds multiple polymeric core particles. That is, the polymeric composite particle contains multiple polymeric core particles within a common shell layer (coating layer).

The polymeric core particles, including loaded polymeric core particles, are not tacky. This increases the likelihood that multiple polymeric core particles will not adhere together before or during application of the coating layer. That is, the lack of tackiness of the porous core particles increases the likelihood that the coating layer will be positioned around a single polymeric core particle rather than around multiple polymeric core particles.

The coating layer is formed by mixing a coating solution or coating dispersion with the porous polymeric core particle (e.g., loaded polymeric core particles). The coating solution or coating dispersion can have any desired percent solids that allow good mixing with the polymeric core particles. In many embodiments, the maximum percent solids often correspond to the coating solution or dispersion having the highest viscosity that can be pumped. High solids can be desirable because less solvent or water needs to be removed during the process of forming the coating layer. If the percent solids are too high, however, it is more likely that the coating layer will surround multiple polymeric core particles. In many embodiments, dilute coating solutions or coating dispersions are used to increase the likelihood of forming polymeric composite particles containing a single polymeric core particle.

The coating solution or coating dispersion often contains at least 5 weight percent, at least 10 weight percent, at least 15 weight percent, or at least 20 weight percent based solids. The weight percent solids corresponds to the weight percent thermoplastic polymer and/or wax in the coating solution or coating dispersion. The weight percent solids can be up to 70 weight percent or even higher, up to 60 weight percent, up to 50 weight percent, up to 40 weight percent, or up to 30 weight percent. For example, the weight percent solids can be in a range of 10 to 70 weight percent, 20 to 60 weight percent, 20 to 50 weight percent, or 20 to 40 weight percent.

Spray drying (spray coating and drying) or similar processes such as fluidized bed coating and drying that can result in the formation of a coating layer with relatively uniform thickness around the polymeric core particles is often considered to be preferable. If conditions are selected appropriately, these processes can be used to provide polymeric composite particles having a single rather than multiple porous polymeric core particles. That is, the polymeric composite particles have a core-shell arrangement with a coating layer around a single porous polymeric core particle.

With spray drying, the polymeric core particles (e.g., polymeric core particles loaded with a biologically active agent) are mixed with the coating solution or coating dispersion to form a slurry. This slurry is then pumped to a drying chamber that contains an atomizer to form droplets and a drying gas. Some common types of atomization include rotary wheel (centrifugal) atomization, single-fluid/pressure nozzle (hydraulic) atomization, two-fluid nozzle (pneumatic) atomization, and ultrasonic atomization. The product, which is the dried polymeric composite particles, can be collected by various means such as by gravity or by using a cyclone, filter and bag, electrostatic separation, or the like.

Although any suitable atomization process can be used, two-fluid nozzle atomizers are often used. With these atomizers, a primary fluid (e.g., the slurry) is pumped through a small orifice and a second fluid, which is typically air or nitrogen, is supplied near the small orifice to further atomize the primary fluid. Increasing the ratio of the secondary fluid to the primary fluid usually decreases the slurry droplet size and increases the likelihood of having a single polymeric core particle within the coating layer.

The two-fluid systems may have either internal mixing (the second fluid is introduced into the primary fluid before exiting the final orifice) or external mixing (the second fluid is introduced after the primary fluid exits the final orifice). Multiple different configurations can be used for introducing the second fluid relative to the primary fluid. For example, the configuration can be a round spray (concentric ring of the second fluid surrounding the primary fluid orifice), conical/hollow spray, angle/flat spray, swirl spray, or the like. Atomizers with these different configurations are available from various suppliers such as Spraying Systems Co. (Wheaton, Ill., USA).

Numerous options can be used for the flow of the bulk drying gas into and out of the drying chamber. To maintain sufficient thermal energy and to provide a drying gas with sufficient drying capacity (e.g., low dew point), the drying air is usually continuously cycled through the drying chamber. The main classes of flow patterns of the drying gas relative to the atomized droplets (input material) are co-current flow, counter-current flow, and mixed flow. Co-current flow involves the input material traveling in the same direction as the bulk drying gas; this is often embodied as input material travelling downward immediately after atomization (e.g. being sprayed downward) along with the downward-travelling bulk drying gas. Counter-current flow involves the input material travelling in the opposite direction to the bulk drying gas; this is often embodied as input material travelling downward immediately after atomization (e.g. being sprayed downward) while the bulk drying gas is travelling upward. Mixed flow is a combination of co- and counter-current flow, where the input material is travelling in the same direction as the bulk drying gas in some regions, but in the opposite direction in other regions. Most often this flow pattern is seen when the input material is being atomized in an upward direction, where the input material initially travels upward from the energy imparted on it by atomization, but is subsequently pulled downward by gravity. Because the input material travels in two directions, the bulk drying gas will travel with the input material in some places and against the input material in others, regardless of whether the bulk drying gas is traveling downward or upward.

The drying temperature is usually selected based on the composition of the loaded polymeric core particles and the coating solution or dispersion. In many embodiments, the bulk drying gas at the outlet of the drying chamber has a temperature near the boiling point of the water or organic solvent used in the slurry (in the coating solution or dispersion) to ensure that adequate drying occurs. This does result, however, in the dried solids reaching a temperature that is near the boiling point of the water or organic solvent. In most instances, this can be beneficial because it minimizes residual liquids, which can lead to improved flowability, reduced hazards from volatile organic solvents being present, and reduction of unnecessary mass.

For some polymeric composite particles, however, it may be undesirable to use such a high drying temperature. This can be the situation, for example, where any component of the polymeric composite particles has a glass transition temperature, melting temperature, or decomposition temperature near the boiling point of the water or organic solvent contained in the slurry. In particular, care must be taken to prevent or minimize release of the biologically active agent from the polymeric composite particle. In such a situation, the drying temperature is typically reduced below that where any undesirable alteration of the polymeric composite particle can occur. Drying can be accomplished at lower temperatures, for example, by increasing the residence time in the drying chamber, increasing the flow rate of the drying gas, decreasing the evaporative load, or modifying the flow patterns.

Multiple coating layers can be positioned around the porous polymeric core particle. Often, multiple layers are added to provide a thicker coating layer or to alter the release characteristics of the biologically active agent from the porous polymeric composite particle. If multiple coating layers are used, they are usually selected to be compatible with each other. In many embodiments, the same thermoplastic material and/or wax is used to form the multiple coating layers.

The coating layer can have any desired thickness. In some embodiments, the thickness is at least 0.1 micrometers, at least 0.2 micrometers, at least 0.5 micrometers, at least 0.75 micrometers, or at least 1.0 micrometers. The thickness can be up to 5 micrometers or more, up to 4 micrometers, up to 3 micrometers, or up to 2 micrometers. The release profile of the biologically active agent within the polymeric composite particle usually can be controlled by the thickness of the coating layer. That is, the greater the thickness, the slower the release rate of the biologically active agent through the coating layer. On the other hand, the release rate of the biologically active agent can be increased by decreasing the coating layer thickness.

As an alternative to spray drying or similar processes, a mixture of the polymeric core particles (e.g., the loaded polymeric core particles) and either the coating solution or the coating dispersion can be spread out into a thin layer for drying purposes. Any suitable drying method can be used. The dried layer can then be broken apart to provide the polymeric composite particles. For example, the dried layer can be placed within a blender to separate the particles from each other. The percent solids in the thin layer are typically relatively low to decrease the likelihood of having multiple polymeric core particles within the same porous polymeric composite particle. This method can be used when relatively uniform coating layer thicknesses are not necessary or where a variety of coating thicknesses may be desired to provide a wider distribution of release rates for biologically active agent. Additionally, this method can be used when it may be beneficial to have multiple polymeric core particles surrounded by the same coating layer to provide a distribution of release rates.

The polymeric composite particle typically contains at least 20 weight percent porous polymeric core particle, at least 0.1 weight percent biologically active agent, and at least 10 weight percent coating layer based on the total weight of the porous polymeric composite particle. In some examples, the polymeric composite particle can contain at least 30 weight percent porous polymeric core particle, at least 0.5 weight percent biologically active agent, and at least 20 weight percent coating layer. In other examples, the polymeric composite particle can contain at least 40 weight percent porous polymeric core particle, at least 1 weight percent biologically active agent, and at least 30 weight percent coating layer.

The polymeric composite particle typically contains up to 90 weight percent porous polymeric core particle, up to 40 weight percent biologically active agent, and up to 80 weight percent coating layer. In some example, the polymeric composite particle can contain up to 80 weight percent porous polymeric core particle, up to 30 weight percent biologically active agent, and up to 70 weight percent coating layer. In other examples, the polymeric composite particle can contain up to 70 weight percent porous polymeric core particle, up to 20 weight percent biologically active agent, and up to 60 weight percent coating layer.

In some embodiments, the polymeric composite particle contains 20 to 90 weight percent porous polymeric core particle, 0.1 to 40 weight percent biologically active agent, and 10 to 80 weight percent coating layer. In some examples, the polymeric composite particle contains 30 to 80 weight percent porous polymeric particle, 0.1 to 40 weight percent biologically active agent, and 20 to 70 weight percent coating layer. In other examples, the polymeric composite particle contains 40 to 70 weight percent porous polymeric particle, 1 to 40 weight percent biologically active agent, and 30 to 60 weight percent coating layer.

The porous composite particles can be used directly in various applications to store and deliver various biologically active agents. These porous composite particles can be used alone to provide delivery of the biologically active agents. For example, the porous composite particles can be placed in the ground near a plant to release a biologically active agent. Alternatively, the porous composite particles can be placed in various compositions such as a medicament, lotion, gel, cream, ointment, liquid, or the like to provide release of the biologically active agent over time. Such compositions can contain up to 50 weight percent or more of the porous polymeric composite particles.

In some embodiments, the polymeric composite particles are combined with a polymeric binder to prepare a coating composition. The coating composition can be applied to any suitable substrate surface. Suitable binders include, for example, polyurethanes, polyacrylates, poly(ethylene glycols), polyesters, poly(lactic acid), alginic acid, cellulose or cellulose derivatives, and the like. The binders can be linear or can be crosslinked. In some embodiments, binders are selected that can chemically react with the groups present on the coating layer of the porous polymeric composite particles, on the substrate, or both.

The amount of binder in the coating composition is often selected to be an amount sufficient to form a film on the substrate but not enough to cover all of the pores on the surface of the polymeric composite particles. Typically, the coating composition contains up to 85 weight percent or more of the polymeric composite particles. For example, the coating composition can contain up to 80 weight percent, up to 70 weight percent, or up to 60 weight percent polymeric composite particles. The coating compositions typically contain at least 10 weight percent, at least 20 weight percent, at least 30 weight percent, or at least 40 weight percent polymeric composite particles. In some embodiments, the coatings contain 20 to 85 weight percent, 40 to 85 weight percent, 50 to 85 weight percent, or 60 to 85 weight percent of the polymeric composite particles based on a total weight of the coating composition. Adding more polymeric composite particles tends to increase the amount of biologically active agent that can be stored and delivered.

The coating composition can be applied to any suitable substrate. In some embodiments, the substrate is porous. For example, the substrate can be fibrous and the fibrous substrate can be woven or non-woven. The polymeric composite particles can be distributed on a surface of the fibrous substrate, distributed throughout the fibrous substrate, or both. The fibers used in the fibrous substrate can be constructed of any suitable material and is often a combination of one of more materials. In some embodiments, at least one of the fibers used in the fibrous substrate has groups that can interact with a polymeric binder that is used in a coating composition that contains the polymeric composite particles.

In another aspect, a multilayer polymeric particle is provided. This particle is similar to the composite polymeric particles described above except that no biologically active agent is positioned within the polymeric core particle. The multilayer polymeric particle is one prepared without loading the polymeric core particle with the biological agent or is the particle that remains after complete release of the biologically active agent from the composite polymeric particle.

The multilayer polymeric particle includes a) a porous polymeric core and b) a coating layer around the porous polymeric core, wherein the coating layer comprises a thermoplastic polymer, a wax, or a mixture thereof. The porous polymeric core contains a polymerized product of a reaction mixture that includes i) a first phase and ii) a second phase dispersed in the first phase, wherein a volume of the first phase is greater than a volume of the second phase. The first phase includes 1) water and a polysaccharide dissolved in the water or 2) a surfactant and a compound of Formula (I)

where the variable n is an integer equal to at least 1. The second phase includes 1) a monomer composition comprising a first monomer of Formula (II)

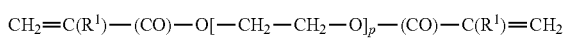

wherein p is an integer equal to at least 1 and $R^1$ is hydrogen or alkyl and 2) a poly(propylene glycol) having a weight average molecular weight of at least 500 grams/mole, wherein the poly(propylene glycol) is removed from the polymerized product to provide the porous polymeric core.

All of the components and methods used to form the multilayer polymeric particle are the same as those described for the composite particle except that no biologically active agent is used.

Various embodiments are provided that are composite polymeric particles or methods of delivering a biologically active agent using a composite polymeric particle.

Embodiment 1 is a polymeric composite particle that includes a) a porous polymeric core, b) a biologically active agent positioned within the porous polymeric core, wherein the biologically active agent is not covalently bonded to the porous polymeric core, and c) a coating layer around the porous polymeric core, wherein the coating layer comprises a thermoplastic polymer, a wax, or a mixture thereof. The porous polymeric core contains a polymerized product of a reaction mixture that includes i) a first phase and ii) a second phase dispersed in the first phase, wherein a volume of the first phase is greater than a volume of the second phase. The first phase includes either 1) water and a polysaccharide dissolved in the water or 2) a surfactant and a compound of Formula (I)

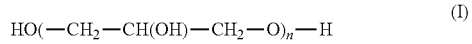

where the variable n is an integer equal to at least 1. The second phase includes 1) a monomer composition comprising a first monomer of Formula (II)

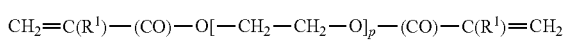

wherein p is an integer equal to at least 1 and $R^1$ is hydrogen or alkyl and 2) a poly(propylene glycol) having a weight average molecular weight of at least 500 grams/mole, wherein the poly(propylene glycol) is removed from the polymerized product to provide the porous polymeric core.

Embodiment 2 is the polymeric composite particle of embodiment 1, wherein the polymeric composite particle has a core-shell configuration with the core being the porous polymeric core and the shell being the coating layer.

Embodiment 3 is the polymeric composite particle of embodiment 1 or 2, wherein the first phase comprise water and 10 to 30 weight percent polysaccharide based on a total weight of the first phase. The polysaccharide is dissolved in the water.

Embodiment 4 is the polymeric composite particle of embodiment 1 or 2, wherein the first phase comprises a nonionic surfactant and the compound of Formula (I).

Embodiment 5 is the polymeric composite of embodiment 4, wherein the compound of Formula (I) is glycerol.

Embodiment 6 is the polymeric composite particle of any one of embodiments 1 to 5, wherein the monomer composition further comprises a second monomer having one (meth)acryloyl group.

Embodiment 7 is the polymeric composite particle of any one of embodiments 1 to 6, wherein the monomer composition further comprises a second monomer of Formula (III).

In Formula (III), $R^1$ is hydrogen or methyl; Y is a single bond, alkylene, oxyalkylene, or poly(oxyalkylene); and $R^2$ is a carbocyclic group or heterocyclic group.

Embodiment 8 is the polymeric composite particle of embodiment 6 or 7, wherein the second monomer of Formula (III) is benzyl (meth)acrylate, 2-phenoxyethyl (meth)acrylate, isobornyl (meth)acrylate, tetrahydrofurfuryl (meth)acrylate, 3,3,5-trimethylcyclohexyl (meth)acrylate, or ethoxylated nonyl phenol acrylate.

Embodiment 9 is the polymeric composite particle of embodiments 1 to 8, wherein the monomer composition further comprises a second monomer of Formula (IV).

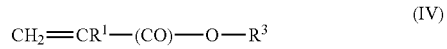

In Formula (IV), $R^1$ is hydrogen or methyl; $R^3$ is a linear or branched alkyl.

Embodiment 10 is the polymeric composite particle of embodiment 9, wherein the second monomer of Formula (IV) is methyl (meth)acrylate, ethyl (meth)acrylate, n-propyl (meth)acrylate, isopropyl (meth)acrylate, n-butyl (meth)acrylate, isobutyl (meth)acrylate, n-pentyl (meth)acrylate, 2-methylbutyl (meth)acrylate, n-hexyl (meth)acrylate, 4-methyl-2-pentyl (meth)acrylate, 2-ethylhexyl (meth)acrylate, 2-methylhexyl (meth)acrylate, n-octyl (meth)acrylate, isooctyl (meth)acrylate, 2-octyl (meth)acrylate, isononyl (meth)acrylate, isoamyl (meth)acrylate, n-decyl (meth)acrylate, isodecyl (meth)acrylate, 2-propylheptyl (meth)acrylate, isotridecyl (meth)acrylate, isostearyl (meth)acrylate, octadecyl (meth)acrylate, 2-octyldecyl (meth)acrylate, dodecyl (meth)acrylate, lauryl (meth)acrylate, or heptadecanyl (meth)acrylate.

Embodiment 11 is the polymeric composite particle of embodiments 1 to 10, wherein the monomer composition further comprises a second monomer of Formula (V).

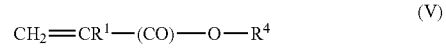

In Formula (V), $R^1$ is hydrogen or methyl; $R^4$ is an alkyl substituted with one or more hydroxyl groups or groups of formula —$(CH_2CH_2O)_qCH_2CH_2OH$ where q is an integer equal to at least 1.

Embodiment 12 is the polymeric composite particle of embodiment 11, wherein the monomer of Formula (V) is 2-hydroxyethyl (meth)acrylate, 2-hydroxypropyl (meth)acrylate, 3-hydroxypropyl (meth)acrylate, and 4-hydroxybutyl (meth)acrylate), 2-hydroxylbutyl (meth)acrylate, polyethylene glycol mono(meth)acrylate, or glycol mono(meth)acrylate.

Embodiment 13 is the polymeric composite particle of any one of embodiments 1 to 11, wherein the monomer composition further comprises a second monomer of Formula (VI).

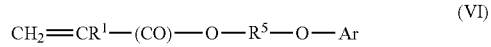

(VI)

In Formula (VI), $R^1$ is hydrogen or methyl; $R^5$ is an alkylene substituted with at least one hydroxyl group; and Ar is an aryl group having 6 to 10 carbon atoms.

Embodiment 14 is the polymeric composite particle of embodiment 13, wherein the second monomer of Formula (VI) is 2-hydroxy-2-phenoxypropyl (meth)acrylate.

Embodiment 15 is the polymeric composite particle of any one of embodiments 1 to 14, wherein the monomer composition further comprises a second monomer of Formula (VII) or a salt thereof.

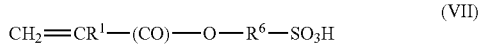

(VII)

In Formula (VIII), $R^1$ is hydrogen or methyl; and $R^6$ is an alkylene.

Embodiment 16 is the polymeric composite particle of embodiment 15, wherein the second monomer of Formula (VII) is sulfoethyl (meth)acrylate or sulfopropyl (meth)acrylate.

Embodiment 17 is the polymeric composite particle of any one of embodiments 1 to 6, wherein the monomer composition further comprises the monomer of Formula (II), a monomer of Formula (III), and a monomer of Formula (VII) of salt thereof.

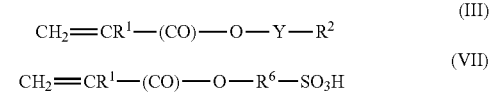

In Formula (III), $R^1$ is hydrogen or methyl; Y is a single bond, alkylene, oxyalkylene, or poly(oxyalkylene); and $R^2$ is a carbocyclic group or heterocyclic group. In Formula (VII), $R^1$ is hydrogen or methyl; and $R^6$ is an alkylene.

Embodiment 18 is the polymeric composite particle of embodiment 17, wherein the monomer composition comprises 20 to 80 weight percent monomer of Formula (II), 20 to 80 weight percent monomer of Formula (III), and 1 to 20 weight percent monomer of Formula (VII).

Embodiment 19 is the polymeric composite particle of embodiment 18, wherein the monomer composition comprises 40 to 60 weight percent monomer of Formula (II), 40 to 60 weight percent monomer of Formula (III), and 1 to 10 weight percent monomer of Formula (VII).

Embodiment 20 is the polymeric composite particle of any one of embodiments 1 to 18, wherein the polymeric core has an average diameter in a range of 1 to 200 micrometers.

Embodiment 21 is the polymeric composite particle of embodiment 20, wherein the polymeric core has pores having an average size in a range of 1 to 200 nanometers.

Embodiment 22 is the polymeric composite particle of any one of embodiments 1 to 21, wherein the biologically active agent is a herbicides, insecticides, fungicides, or mixture thereof.

Embodiment 23 is the polymeric composite particle of any one of embodiments 1 to 22, wherein the coating layer comprises a silicone-based thermoplastic polymer, (meth)acrylate-based thermoplastic polymer, olefin-based thermoplastic polymer, styrene-based thermoplastic polymer, or a phenoxy-based resin.

Embodiment 24 is the polymeric composite particle of any one of embodiments 1 to 22, wherein the coating layer comprises animal wax, vegetable wax, petroleum wax, hydrogenated vegetable oil, or polyethylene.

Embodiment 25 is the polymeric composite particle of any one of embodiments 1 to 24, wherein the coating layer has a thickness in a range of 0.1 micrometers to 5 micrometers.

Embodiment 26 is the polymeric composite particle of any one of embodiment 1 to 24, wherein the polymeric composite particle comprises 20 to 90 weight percent porous polymeric core, 0.1 to 40 weight percent biologically active agent, and 10 to 80 weight percent coating layer.

Embodiment 27 is a method of delivering a biologically active agent. The method includes providing a polymeric composite particle that includes a) a porous polymeric core, b) a biologically active agent positioned within the porous polymeric core, wherein the biologically active agent is not covalently bonded to the porous polymeric core, and c) a coating layer around the porous polymeric core, wherein the coating layer comprises a thermoplastic polymer, a wax, or a mixture thereof. The method further includes releasing the biologically active agent from the polymeric composite particle by diffusion through the coating layer. The porous polymeric core contains a polymerized product of a reaction mixture that includes i) a first phase and ii) a second phase dispersed in the first phase, wherein a volume of the first phase is greater than a volume of the second phase. The first phase includes either 1) water and a polysaccharide dissolved in the water or 2) a surfactant and a compound of Formula (I)

(I)

where the variable n is an integer equal to at least 1. The second phase includes 1) a monomer composition comprising a first monomer of Formula (II)

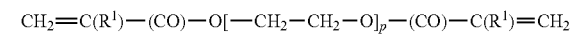

(II)

wherein p is an integer equal to at least 1and $R^1$ is hydrogen or alkyl and 2) a poly(propylene glycol) having a weight average molecular weight of at least 500 grams/mole, wherein the poly(propylene glycol) is removed from the polymerized product to provide the porous polymeric core.

Embodiment 28 is the method of embodiment 27, wherein the first phase comprise water and 10 to 30 weight percent polysaccharide based on a total weight of the first phase.

Embodiment 29 is the method of embodiment 27, wherein the first phase comprises the compound of Formula (I) and a nonionic surfactant.

Embodiment 30 is the method of any one of embodiments 27 to 29, wherein providing the polymeric composite particle comprises forming the porous polymeric core; positioning the biologically active agent within the porous polymeric core to form a loaded polymeric particle; and depositing the coating layer around the loaded polymeric particle.

Embodiment 31 is the method of embodiment 30, wherein depositing the coating layer comprises preparing a coating solution or a coating dispersion, mixing the loaded polymeric particle with the coating solution or coating dispersion to form a slurry, and drying the slurry by spray drying or fluidized bed drying.

Embodiment 32 is the method of any one of embodiments 27 to 31, wherein the polymeric composite particle has a core-shell configuration with the core being the porous polymeric core and the shell being the coating layer.

Embodiment 33 is the method of any one of embodiments 27 to 31, wherein the polymeric composite particle has a coating layer around a single porous polymer core.

Embodiment 34 is the method of any one of embodiments 27 to 31, wherein the polymeric composite particle has a coating layer around multiple porous polymeric cores.

Embodiment 35 is the method of any one of embodiments 27 to 34, wherein the monomer composition further comprises a second monomer having one (meth)acryloyl group.

Embodiment 36 is the method of any one of embodiments 27 to 35, wherein the monomer composition further comprises a second monomer of Formula (III), Formula (IV), or both.

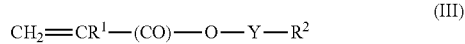   (III)

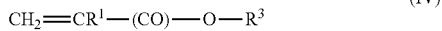   (IV)

In Formula (III), $R^1$ is hydrogen or methyl; Y is a single bond, alkylene, oxyalkylene, or poly(oxyalkylene); and $R^2$ is a carbocyclic group or heterocyclic group. In Formula (IV), $R^1$ is hydrogen or methyl; $R^3$ is a linear or branched alkyl.

Embodiment 37 is the method of any one of embodiments 27 to 36, wherein the monomer composition further comprises a second monomer of Formula (V).

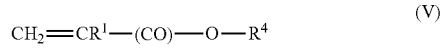   (V)

In Formula (V), $R^1$ is hydrogen or methyl; $R^4$ is an alkyl substituted with one or more hydroxyl groups or groups of formula $-(CH_2CH_2O)_qCH_2CH_2OH$ where q is an integer equal to at least 1.

Embodiment 38 is the method of any one of embodiments 27 to 37, wherein the monomer composition further comprises a second monomer of Formula (VI).

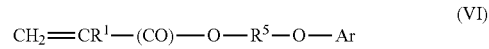   (VI)

In Formula (VI), $R^1$ is hydrogen or methyl; $R^5$ is an alkylene substituted with at least one hydroxyl group; and Ar is an aryl group having 6 to 10 carbon atoms.

Embodiment 39 is the method of any one of embodiments 27 to 38, wherein the monomer composition further comprises a second monomer of Formula (VII) or salt thereof.

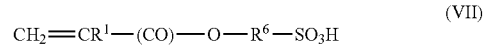   (VII)

In Formula (VIII), $R^1$ is hydrogen or methyl; and $R^6$ is an alkylene.

Embodiment 40 is the method of any one of embodiments 27 to 39, wherein the monomer composition comprises the first monomer of Formula (II), a second monomer of Formula (III), and another second monomer of Formula (VII) of a salt thereof.

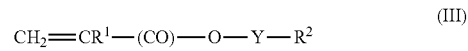   (III)

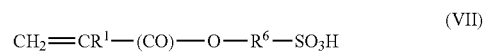   (VII)

In Formula (III), $R^1$ is hydrogen or methyl; Y is a single bond, alkylene, oxyalkylene, or poly(oxyalkylene); and $R^2$ is a carbocyclic group or heterocyclic group. In Formula (VII), $R^1$ is hydrogen or methyl; and $R^6$ is an alkylene.

Embodiment 41 is the method of embodiment 40, wherein the monomer composition comprises 20 to 80 weight percent monomer of Formula (II), 20 to 80 weight percent monomer of Formula (III), and 1 to 20 weight percent monomer of Formula (VII).

Embodiment 42 is the method of embodiment 41, wherein the monomer composition comprises 40 to 60 weight percent monomer of Formula (II), 40 to 60 weight percent monomer of Formula (III), and 1 to 10 weight percent monomer of Formula (VII).

Embodiment 43 is the method of any one of embodiments 27 to 42, wherein the polymeric core has an average diameter in a range of 1 to 200 micrometers.

Embodiment 44 is the method of embodiment 43, wherein the polymeric core has pores having an average size in a range of 1 to 200 nanometers.

Embodiment 45 is the method of any one of embodiments 27 to 44, wherein the biologically active agent is a herbicides, insecticides, fungicides, or mixture thereof.

Embodiment 46 is the method of any one of embodiments 27 to 45, wherein the coating layer comprises a silicone-based thermoplastic polymer, (meth)acrylate-based thermoplastic polymer, olefin-based thermoplastic polymer, styrene-based thermoplastic polymer, or a phenoxy-based resin.

Embodiment 47 is the method of any one of embodiments 27 to 46, wherein the coating layer comprises animal wax, vegetable wax, petroleum wax, hydrogenated vegetable oil, or polyethylene.

Embodiment 48 is the method of any one of embodiments 27 to 47, wherein the coating layer has a thickness in a range of 0.1 micrometers to 5 micrometers.

Embodiment 49 is the method of any one of embodiments 27 to 48, wherein the polymeric composite particle comprises 20 to 90 weight percent porous polymeric core, 0.1 to 40 weight percent biologically active agent, and 10 to 80 weight percent coating layer.

Embodiment 50 is a polymeric composite particle that includes a) a porous polymeric core, b) a biologically active agent positioned within the porous polymeric core, wherein the biologically active agent is not covalently bonded to the porous polymeric core, and c) a coating layer around the porous polymeric core, wherein the coating layer comprises a thermoplastic polymer, a wax, or a mixture thereof. The porous polymeric core contains a polymerized product of a reaction mixture that includes i) a first phase and ii) a second phase dispersed in the first phase, wherein a volume of the first phase is greater than a volume of the second phase. The first phase includes either 1) water and a polysaccharide dissolved in the water or 2) a surfactant and a compound of Formula (I)

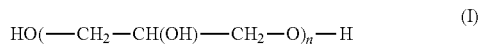

where the variable n is an integer equal to at least 1. The second phase includes 1) a monomer composition and 2) a poly(propylene glycol) having a weight average molecular weight of at least 500 grams/mole, wherein the poly(propylene glycol) is removed from the polymerized product to provide the porous polymeric core. The monomer composition comprises a monomer of Formula (II) and a monomer of Formula (VII) or salt thereof.

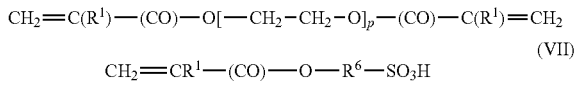

In Formula (II), the variable p is an integer equal to at least 1 and $R^1$ is hydrogen or alkyl. In Formula (VII), $R^1$ is hydrogen or methyl; and $R^6$ is an alkylene.

Embodiment 51 is the polymeric composite particle of embodiment 50, wherein the monomer composition further comprises a monomer of Formula (III).

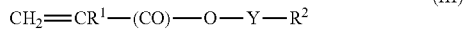

In Formula (III), $R^1$ is hydrogen or methyl; Y is a single bond, alkylene, oxyalkylene, or poly(oxyalkylene); and $R^2$ is a carbocyclic group or heterocyclic group.

Embodiment 52 is the polymeric composite particle of embodiment 51, wherein the first phase comprise water and 10 to 30 weight percent polysaccharide based on a total weight of the first phase.

Embodiment 53 is the polymeric composite particle of embodiment 51, wherein the first phase comprises the compound of Formula (I) and a nonionic surfactant.

Embodiment 54 is the polymeric composite particle of Embodiment 53, wherein the compound of Formula (I) is glycerol.

Embodiment 55 is the polymeric composite particle of Embodiment 50 or 54, wherein the monomer of Formula (III) is benzyl (meth)acrylate, 2-phenoxyethyl (meth)acrylate, isobornyl (meth)acrylate, tetrahydrofurfuryl (meth)acrylate, 3,3,5-trimethylcyclohexyl (meth)acrylate, or ethoxylated nonyl phenol acrylate.

Embodiment 56 is the polymeric composite particle of any one of Embodiments 50 to 55, wherein the monomer of Formula (VII) is sulfoethyl (meth)acrylate or sulfopropyl (meth)acrylate.

Embodiment 57 is the polymeric composite particle of any one of Embodiments 50 to 56, wherein the monomer of Formula (III) is 2-phenoxy (meth)acrylate and the monomer of Formula (VII) is sulfoethyl (meth)acrylate.

Embodiment 58 is the polymeric composite particle of any one of embodiments 50 to 57 wherein the monomer composition comprises 20 to 80 weight percent monomer of Formula (II), 20 to 80 weight percent monomer of Formula (III), and 1 to 20 weight percent monomer of Formula (VII).

Embodiment 59 is the polymeric composite particle any one of embodiments 50 to 58, wherein the monomer composition comprises 40 to 60 weight percent monomer of Formula (II), 40 to 60 weight percent monomer of Formula (III), and 1 to 10 weight percent monomer of Formula (VII).

Embodiment 60 is the polymeric composite particle of any one of embodiments 50 to 59, wherein the polymeric has an average diameter in a range of 1 to 200 micrometers.

Embodiment 61 is the polymeric composite particle of any one of embodiment 50 to 60, wherein the polymeric core has pores having an average size in a range of 1 to 200 nanometers.

Embodiment 62 is the polymeric composite particle of any one of embodiments 50 to 61, wherein the biologically active agent is a herbicides, insecticides, fungicides, or mixture thereof.

Embodiment 63 is the polymeric composite particle of any one of embodiments 50 to 62, wherein the coating layer comprises a silicone-based thermoplastic polymer, (meth)acrylate-based thermoplastic polymer, olefin-based thermoplastic polymer, styrene-based thermoplastic polymer, or a phenoxy-based resin.

Embodiment 64 is the polymeric composite particle of any one of embodiments 50 to 63, wherein the coating layer comprises animal wax, vegetable wax, petroleum wax, hydrogenated vegetable oil, or polyethylene.

Embodiment 65 is the polymeric composite particle of any one of embodiments 50 to 64, wherein the coating layer has a thickness in a range of 0.1 micrometers to 5 micrometers.

Embodiment 66 is the polymeric composite particle of any one of embodiments 50 to 65, wherein the polymeric composite particle comprises 20 to 90 weight percent porous polymeric core, 0.1 to 40 weight percent biologically active agent, and 10 to 80 weight percent coating layer.

Embodiment 67 is a multilayer polymeric particle that includes a) a porous polymeric core and b) a coating layer around the porous polymeric core, wherein the coating layer comprises a thermoplastic polymer, a wax, or a mixture thereof. The porous polymeric core contains a polymerized product of a reaction mixture that includes i) a first phase and ii) a second phase dispersed in the first phase, wherein a volume of the first phase is greater than a volume of the second phase. The first phase includes either 1) water and a polysaccharide dissolved in the water or 2) a surfactant and a compound of Formula (I)

$$HO(\!-\!CH_2\!-\!CH(OH)\!-\!CH_2\!-\!O)_n\!-\!H \qquad (I)$$

where the variable n is an integer equal to at least 1. The second phase includes 1) a monomer composition comprising a first monomer of Formula (II)

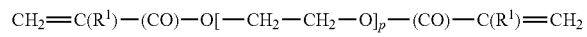
(II)

wherein p is an integer equal to at least 1 and $R^1$ is hydrogen or alkyl and 2) a poly(propylene glycol) having a weight average molecular weight of at least 500 grams/mole, wherein the poly(propylene glycol) is removed from the polymerized product to provide the porous polymeric core.

Embodiment 68 is the multilayer polymeric particle of embodiment 67, wherein the polymeric composite particle has a core-shell configuration with the core being the porous polymeric core and the shell being the coating layer.

Embodiment 69 is the multilayer polymeric particle of embodiment 67 or 68, wherein the first phase comprise water and 10 to 30 weight percent polysaccharide based on a total weight of the first phase. The polysaccharide is dissolved in the water.

Embodiment 70 is the multilayer polymeric particle of embodiment 67 or 68, wherein the first phase comprises a nonionic surfactant and the compound of Formula (I).

Embodiment 71 is the multilayer polymeric particle of embodiment 70, wherein the compound of Formula (I) is glycerol.

Embodiment 72 is the multilayer polymeric particle of any one of embodiments 67 to 71, wherein the monomer composition further comprises a second monomer having one (meth)acryloyl group.

Embodiment 73 is the multilayer polymeric particle of any one of embodiments 67 to 72, wherein the monomer composition further comprises a second monomer of Formula (III).

(III)

In Formula (III), $R^1$ is hydrogen or methyl; Y is a single bond, alkylene, oxyalkylene, or poly(oxyalkylene); and $R^2$ is a carbocyclic group or heterocyclic group.

Embodiment 74 is the multilayer polymeric particle of any one of embodiments 67 to 73, wherein the monomer composition further comprises a second monomer of Formula (IV).

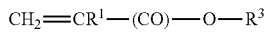
(IV)

In Formula (IV), $R^1$ is hydrogen or methyl; $R^3$ is a linear or branched alkyl.

Embodiment 75 is the multilayer polymeric particle of any one of embodiments 67 to 74, wherein the monomer composition further comprises a second monomer of Formula (V).

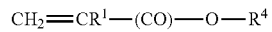
(V)

In Formula (V), $R^1$ is hydrogen or methyl; $R^4$ is an alkyl substituted with one or more hydroxyl groups or a group of formula $—(CH_2CH_2O)_qCH_2CH_2OH$ where q is an integer equal to at least 1.

Embodiment 76 is the multilayer polymeric particle of any one of embodiments 67 to 75, wherein the monomer composition further comprises a second monomer of Formula (VI).

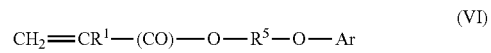
(VI)

In Formula (VI), $R^1$ is hydrogen or methyl; $R^5$ is an alkylene substituted with at least one hydroxyl group; and Ar is an aryl group having 6 to 10 carbon atoms.

Embodiment 77 is the multilayer polymeric particle of any one of embodiments 67 to 76, wherein the monomer composition further comprises a second monomer of Formula (VII) or a salt thereof.

(VII)

In Formula (VIII), $R^1$ is hydrogen or methyl; and $R^6$ is an alkylene.

Embodiment 78 is the multilayer polymeric particle of any one of embodiments 67 to 77, wherein the monomer composition further the monomer of Formula (II), a monomer of Formula (III), and a monomer of Formula (VII) or a salt thereof,

(III)
(VII)

In Formula (III), $R^1$ is hydrogen or methyl; Y is a single bond, alkylene, oxyalkylene, or poly(oxyalkylene); and $R^2$ is a carbocyclic group or heterocyclic group. In Formula (VII), $R^1$ is hydrogen or methyl; and $R^6$ is an alkylene.

Embodiment 79 is the multilayer polymeric particle of embodiment 78, wherein the monomer composition comprises 20 to 80 weight percent monomer of Formula (II), 20 to 80 weight percent monomer of Formula (III), and 1 to 20 weight percent monomer of Formula (VII).

Embodiment 80 is the multilayer polymeric particle of any one of embodiments 67 to 79, wherein the polymeric core has an average diameter in a range of 1 to 200 micrometers.

Embodiment 81 is the multilayer polymeric particle of any one of embodiments 67 to 80, wherein the polymeric core has pores having an average size in a range of 1 to 200 nanometers.

Embodiment 82 is the multilayer polymeric particle of any one of embodiments 67 to 81, wherein the coating layer comprises a silicone-based thermoplastic polymer, (meth)acrylate-based thermoplastic polymer, olefin-based thermoplastic polymer, styrene-based thermoplastic polymer, or a phenoxy-based resin.

Embodiment 83 is the multilayer polymeric particle of any one of embodiments 67 to 82, wherein the coating layer comprises animal wax, vegetable wax, petroleum wax, hydrogenated vegetable oil, or polyethylene.

Embodiment 84 is the multilayer polymeric particle of any one of embodiments 67 to 83, wherein the coating layer has a thickness in a range of 0.1 micrometers to 5 micrometers.

Embodiment 85 is the multilayer polymeric particle of any one of embodiment 67 to 84, wherein the polymeric composite particle comprises 20 to 90 weight percent porous polymeric core, 0.1 to 40 weight percent biologically active agent, and 10 to 80 weight percent coating layer.

EXAMPLES

Unless otherwise noted, all chemicals used in the examples can be obtained from Sigma-Aldrich Corp. (Saint Louis, Mo.).

separate 125 mL clear glass jars. 100 mL water (HPLC-grade from B&J) was added to each jar using a volumetric pipette. The sample containers were capped and shaken on a mechanical wrist-action shaker for 0.5 hours, 7 hours, 24 hours, or 48 hours at room temperature. Duplicate samples were prepared for each time point study. Aliquots of the liquid phase (not including undissolved particles) were removed for liquid chromatography-mass spectrometry (LC-MS) analyses.

Reference standards of TMX were also prepared in water in a calibration range of 1.0 to 15.0 micrograms/mL, and these reference standards were also analyzed by LC-MS.

The LC-MS analyses were carried out using an Agilent 6224 LC-TOF system. The LC-TOF was equipped with a dual-spray electrospray ionization (ESI) source that was

TABLE 1

List of materials and suppliers

| Material | Description |
| --- | --- |
| APG 325N | Trade designation for a nonionic alkyl polyglucoside surfactant that is available from Cognis Corp. (Cincinnati, OH, USA) |
| CASTORWAX | Trade designation for a waxy material that is available from Vertellus Performance Materials, Inc. (Greensboro, NC, USA); according to the supplier, glycerol tri-(12-hydroxystearate) is the principle component |
| IBMA/BMA polymer | Copolymer formed from a 50/50 weight percent mixture of isobutyl methacrylate and butyl methacrylate monomers that has a weight average molecular weight of about 200,000 Daltons; this copolymer is available from Scientific Polymer Products, Inc. (New York, NY, USA) |
| IPA | Isopropyl alcohol, which is available from Sigma Aldrich (St. Louis, MO, USA) |
| IRGACURE 819 | Trade designation for the photoinitiator bis(2,4,6-trimethylbenzoyl)-phenylphosphineooxide, which is available from BASF (Florham Park, NJ, USA) |
| PHMB | Polyhexamethylene biguanide, which is available from Arch Chemical (Atlanta, GA, USA) |
| PKHW-34 | Phenoxy resin, which was obtained as a 34 weight percent dispersion in water from InChem (Rock Hill, SC, USA) |
| PMMA | Poly(methyl methacrylate), which was obtained from Polysciences, Inc. (Warrington, PA, USA); according to the supplier, the molecular weight is about 25,000 Daltons based on measurement of viscosity |
| PPG4000 | Polypropylene glycol having a weight average molecular weight of 4000 Daltons and that is available from Alfa Aesar (Ward Hill, MA, USA) |
| SPOx elastomer | A poly(dimethylsiloxane-oxamide) linear copolymer prepared as described below (see Preparatory Example 4). |
| SR 339 | Trade designation for 2-phenoxyethyl acrylate ester available from Sartomer Company, Inc. (Exton, PA, USA) |
| SR 6030P | Trade designation for polyethylene glycol 400 dimethacrylate with a weight average molecular weight of 400 Daltons and that is available from Sartomer Company, Inc. (Exton, PA, USA) |
| 2-Sulfoethyl methacrylate | Monomer that is available from Scientific Polymer, Inc. (Ontario, NY, USA) |
| TMX | Thiamethoxam, an insecticide, available from Sigma-Aldrich (St. Louis, MO, USA) |
| α,ω-bis(aminopropyl)-polydimethylsiloxane diamine | Silicone diamine of the following formula $$H_2N\text{---}\underset{\underset{CH_3}{\mid}}{\overset{\overset{CH_3}{\mid}}{Si}}\text{---}O\text{---}\underset{\underset{CH_3}{\mid}}{\overset{\overset{CH_3}{\mid}}{Si}}\text{---}_n\text{---}O\text{---}\underset{\underset{CH_3}{\mid}}{\overset{\overset{CH_3}{\mid}}{Si}}\text{---}NH_2$$ having an weight average molecular weight of about 25,000 Daltons that was prepared according to the procedure described in Example 2 of U.S. Pat. No. 5,214,119 (Leir et al.) |

Release Test Method for TMX-Loaded Particles or PHMB-Loaded Particles

Release of TMX from TMX-loaded particles (i.e., porous polymeric core particle loaded with TMX) in water was evaluated using the following method. Multiple 10 milligram samples of TMX-loaded particles were weighed into operated in the positive ion full scan mode (m/z in a range from 105 to 1700). Additionally, UV absorption data was acquired using an Agilent 1260 Diode Array Detector on-line before the detection by ESI-MS. The 254 nm signal was used for quantification of TMX. HPLC column: Agilent Eclipse XDB-C18, 150 mm×3.0 mm, 5 micrometer particle size. The HPLC column temperature was set at 40° C. The HPLC mobile phase was solution (A) water with 6 mM ammonium acetate and/or solution (B) acetonitrile-water, 98/2, v/v, with 6 mM ammonium acetate. A gradient method was used. The gradient included a linear change over 15 minutes from an initial mobile phase containing 10 weight percent solution B and 90 weight percent solution A to a final mobile phase containing 100 weight percent solution B. The final mobile phase was used for an additional 15 minutes. The HPLC flow rate was set at 0.5 mL/min. The sample injection volume was 10 microliters. Results were reported as the average of duplicates for each time point (i.e., n=2).

Release of a PHMB from PHMB-loaded particles (i.e., porous polymeric core particle loaded with PHMB) in water was conducted in the same manner as described above for the TMX-loaded particles.

Preparatory Example 1 (PE-1): Preparation of Porous Core Particle

Monomers SR 339 (50 grams), SR 6030P (50 grams) and 2-sulfoethyl methacrylate (5 grams) were mixed with PPG4000 (43 grams) and IRGACURE 819 (250 milligrams). The mixture was stirred vigorously for 20 minutes at about 40° C. to 50° C. This mixture was then added to 750 grams of glycerol previously mixed with 7.5 g of APG 325 N. The mixture was then shear mixed for 20 minutes. The mixture was then spread thin between two sheets of polyethylene terephthalate (PET) and cured with ultraviolet light for 10 to 15 minutes with a 100 Watts, long-wavelength BLACK RAY UV lamp (available from UVP, LLC of Upland, Calif.) situated at about 15 centimeters (6 inches) from the surface of the curing material.

The cured mixture was then dispersed in 500 mL of IPA, shaken for 30 minutes, and centrifuged at 3000 rpm in an EPPENDORF 5810 R centrifuge (available from Eppendorf in Germany). The supernatant was removed and the resulting particles were then re-suspended in another 500 mL of IPA for a second rinse followed by centrifugation, and the supernatant was discarded. The particles were oven-dried overnight at 70° C. FIGS. 1A, 1B, and 1C show SEM images of the dried nano-porous micro-particles (i.e., porous polymeric core particles).

Preparatory Example 2 (PE-2): Preparation of PHMB-Loaded Particles

Porous polymeric core particles (25 grams) made according to PE-1 were imbibed for about 10 minutes with a solution of 125 mg PHMB dissolved in 30 mL of methanol. The resulting particles were then air dried for three hours and then vacuum dried for one hour. The product was PHMB-loaded particles. The theoretical loading was 5 milligrams PHMB per gram of porous polymeric core particles.

Preparatory Example 3 (PE-3): Preparation of TMX-Loaded Particles

Porous polymeric core particles (240 grams) made according to PE-1 were soaked for two hours in a solution of 100 grams of TMX dissolved in 900 grams dichloromethane. The resulting particles were then air dried for 1 hour and oven dried overnight at 40° C. The final product was TMX-loaded particles. The theoretical loading was about 40 weight percent (0.4 grams TMX per gram of porous polymeric core particles).

Preparatory Example 4 (PE-4): Preparation of SPOx Elastomer

A silicone polyoxamide (SPOx) elastomer was prepared in two steps. In the first step, an $\alpha,\omega$-bis(aminopropyl) polydimethylsiloxane diamine with a molecular weight of 25,000 grams/mole was capped with diethyl oxalate to provide an $\alpha,\omega$-oxamido oxalate ester capped precursor. This step was completed by following the general procedure of Preparative Example 1 in U.S. Pat. No. 7,371,464 (Sherman et al.). The diethyl oxalate was used in a molar excess to the diamine to provide the an $\alpha,\omega$-oxamido oxalate ester capped precursor. This precursor was chain-extended into the silicone polyoxamide elastomer using ethylene diamine following the general procedure of Preparative Example 3 in U.S. Pat. No. 7,371,464 (Sherman et al.) with the exception that the above $\alpha,\omega$-oxamido oxalate ester capped precursor was used instead of a mixture of precursors and the reaction time was four days. The mole ratio of precursor to ethylene diamine was 1 to 1. The resulting SPOx elastomer was used neat without determining hardness.

Example 1 (EX-1): SPOx-Coated PHMB-Loaded Particles

The PHMB-loaded particles of PE-2 (25 grams) were mixed with 25 grams of the SPOx polymer from PE-2 dissolved in 500 grams of heptane. This mixture was then spread out in a glass pan and air dried for three hours. The dried product was crushed into small particles (ranging from about 10 to 100 micrometers) with a blender, providing SPOx-coated PHMB-loaded particles. The PHMB loading level was calculated to be about 0.5 weight percent (5 milligrams PHMP per gram of porous polymeric core particles) or about 0.25 weight percent for the polymeric composite particles (SPOx-coated PHMB-loaded particles).

The PHMB-release profiles in water for the PHMB-loaded particles of PE-2 (no coating layer) and the SPOx-coated PHMB-loaded particles of EX-1 were determined using the Release Test Method described above. The results are summarized in Table 2. The values in the table are micrograms of PHMB per mL of extraction solution.

TABLE 2

| | PHMB release over time | | | |
|---|---|---|---|---|
| Sample | 0.1 hour | 0.5 hour | 7 hours | 24 hours |
| PE-2 | 151 micrograms/mL | 134 micrograms/mL | 154 micrograms/mL | 186 micrograms/mL |
| EX-1 | 13 micrograms/mL | 37 micrograms/mL | 69 micrograms/mL | 89 micrograms/mL |

Examples 2A and 2B (EX-2A and EX-2B): Methacrylate-Coated TMX-Loaded Particles

EX-2A material was prepared as follows. A 340 gram sample of the TMX-loaded particles of PE-3 was combined with 272 grams of IBMA/BMA polymer (methacrylate polymer) previously dissolved in 3000 grams of toluene, forming a suspension. This suspension was then spray dried (inlet temperature about 170° C., outlet temperature about 70° C.) to form an approximately 0.75 micrometer methacrylate coating on the TMX-loaded particles. These composite particles theoretically contained 22 weight percent TMX.

EX-2B material was prepared as follows. A 340 gram sample of the TMX-loaded particles of PE-3 was combined with 890 grams of IBMA/BMA polymer previously dissolved in 2000 grams of toluene, forming a suspension. This suspension was then spray dried using a MOBILE MINOR type spray dryer obtained from GEA Process Engineering, Inc. (Colombia, Md.). The spray dryer was operated using co-current flow with two-fluid round spray nozzle atomization, an inlet temperature of about 170° C., and an outlet temperature of about 70° C. to form an approximately 2 micrometer methacrylate coating on the TMX-loaded particles. These composite particles theoretically contained 11 weight percent TMX.

Figure 2:
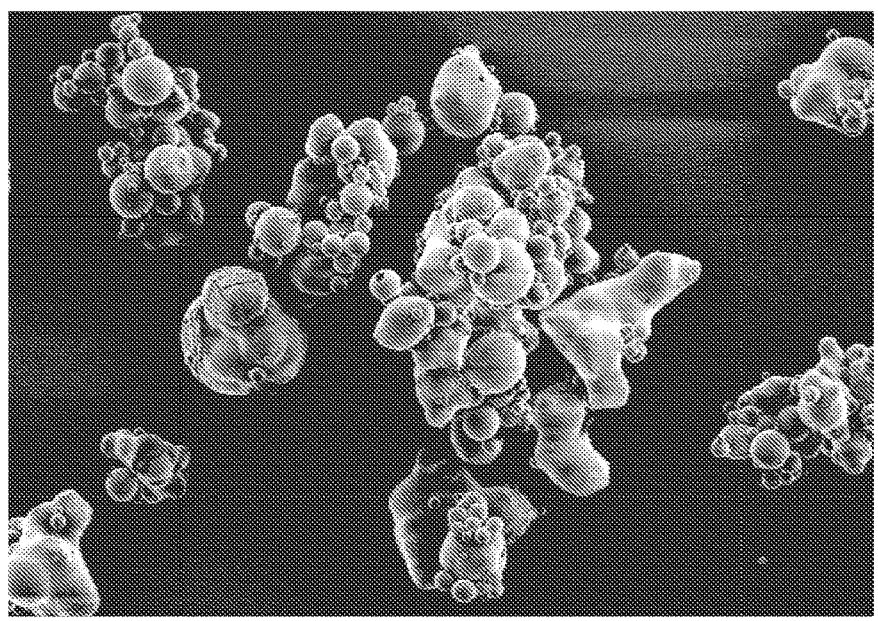
FIG. 2 is a scanning electron micrograph of the porous polymeric composite particles prepared in Example 2B.

FIG. 2 shows an SEM image of the spray-dried particles of EX-2B. Various particle sizes were observed in the SEM image. This suggests that multiple core particles were included in some of the composite particles.

TMX release profiles of the methacrylate-coated TMX-loaded particles of EX-2A and EX-2B were determined using the Release Test Method described above. The results as summarized in Tables 3 and 4, respectively. The TMX % (wt/wt) values in the Tables 3 and 4 indicate the weight percent of TMX extracted based on a total weight of the methacrylate-coated TMX-loaded particles.

TABLE 3

TMX release profile for EX-2A

| Extraction time, hours | TMX % (wt/wt) | Average TMX % (wt/wt) |
|---|---|---|
| 0.5 | 3.39 | 4.1 |
| 0.5 | 4.72 | |
| 7 | 5.75 | 5.2 |
| 7 | 4.75 | |
| 24 | 7.02 | 7.9 |
| 24 | 8.73 | |
| 48 | 8.18 | 8.8 |
| 48 | 9.36 | |

TABLE 4

TMX release profile for EX-2B

| Extraction time, hours | TMX % (wt/wt) | Average TMX % (wt/wt) |
|---|---|---|
| 0.5 | 0.68 | 0.72 |
| 0.5 | 0.75 | |
| 7 | 1.50 | 1.39 |
| 7 | 1.29 | |
| 24 | 1.27 | 1.26 |
| 24 | 1.24 | |
| 48 | 1.48 | 1.21 |
| 48 | 0.94 | |

Example 3 (EX-3): PMMA-Coated TMX-Loaded Particles

A 25 gram sample of the TMX-loaded particles of PE-3 was combined with 25 grams of PMMA pre-dissolved in 80 grams of toluene. This mixture was then spread out in a glass pan and air dried for three hours. The dried product was crushed into small particles with a blender, providing the PMMA-coated TMX-loaded particles. These composite particles theoretically contained about 20 weight percent TMX.

The TMX release profile was determined using the Release Test method described above. The results as summarized in Table 5. The TMX % (wt/wt) values in the Table 5 indicate the weight percent of TMX extracted based on a total weight of the PMMA-coated TMX-loaded particles.

TABLE 5

TMX release profile for EX-3

| Extraction time, hours | TMX % (wt/wt) | Average TMX % (wt/wt) |
|---|---|---|
| 0.5 | 8.30 | 7.4 |
| 0.5 | 6.53 | |
| 7 | 9.67 | 9.3 |
| 7 | 8.90 | |
| 24 | 9.41 | 9.5 |
| 24 | 9.51 | |
| 48 | 9.03 | 9.2 |
| 48 | 9.33 | |

Example 4 (EX-4): Phenoxy-Coated TMX-Loaded Particles

A 25 gram portion of the TMX-loaded particles from PE-3 was added to 181 grams of a mixture of 34 weight percent PKHW-34 phenoxy resin dispersion further diluted an additional 83 grams of distilled water. The resulting dispersion was blended and filtered through cheese cloth. The filtered dispersion was then spray dried in a B-191 mini spray dryer that was obtained from Buchi Laboratory Equipment (Flawil, Switzerland). The spray dryer was operated using a fluid feed rate of approximately 20 grams/minute with an external variable speed positive displacement pump obtained from Cole Palmer (Vernon Hills, Ill., USA), which was model C-11V141X000V00. The inlet and outlet temperatures of the spray dryer were approximately 170° C. and 75° C. respectively. The composite polymeric particles theoretically contained about 11.5 weight percent TMX.

FIG. 3 shows an SEM image of the spray-dried particles of EX-4.

The TMX release profile was determined using the Release Test Method described above. The results are summarized in Table 6. The TMX % (wt/wt) values in the Table 6 indicate the weight percent of TMX extracted based on a total weight of the phenoxy-coated TMX-loaded particles.

TABLE 6

TMX Release Profile for EX-4

| Extraction time, hours | TMX % (wt/wt) | Average TMX % (wt/wt) |
|---|---|---|
| 0.5 | 3.62 | 3.7 |
| 0.5 | 3.80 | |
| 7 | 3.87 | 3.9 |
| 7 | 3.86 | |
| 24 | 3.69 | 3.8 |
| 24 | 3.89 | |
| 48 | 3.59 | 3.6 |
| 48 | 3.68 | |

Example 5 (EX-5): Wax-Coated TMX-Loaded Particles

A 0.4 gram portion of TMX-loaded particles from PE-3 was added to a solution of 2 grams of CASTORWAX dissolved in 8 grams of dichloromethane. This mixture was then spread out in a glass pan and air dried for three hours. The dried product was crushed into small particles with a blender. The composite polymeric particles theoretically contained about 6.7 weight percent TMX.

The TMX-release profile was then determined using the Release Test Method described above. The results as summarized in Table 7. The TMX % (wt/wt) values in the Table 7 indicate the weight percent of TMX extracted based on a total weight of the wax-coated TMX-loaded particles.

TABLE 7

TMX release profile for EX-5

| Extraction time, hours | TMX % (wt/wt) | Average TMX % (wt/wt) |
|---|---|---|
| 0.5 | 3.62 | 3.7 |
| 0.5 | 3.80 | |
| 7 | 3.87 | 3.9 |
| 7 | 3.86 | |
| 24 | 3.69 | 3.8 |
| 24 | 3.89 | |
| 48 | 3.59 | 3.6 |
| 48 | 3.68 | |

What is claimed is:

1. A polymeric composite particle comprising
a) a porous polymeric core particle comprising a washed and dried polymerized product of a reaction mixture comprising:
   i) a first phase comprising either
      1) water and a polysaccharide dissolved in the water; or
      2) a surfactant and a compound of Formula (I)

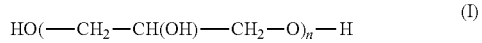

$$HO(-CH_2-CH(OH)-CH_2-O)_n-H \quad (I)$$

wherein n is an integer equal to at least 1, or a mixture thereof; and
   ii) a second phase dispersed in the first phase, wherein a volume of the first phase is greater than a volume of the second phase and wherein the second phase comprises
      1) a monomer composition comprising a first monomer of Formula (II)

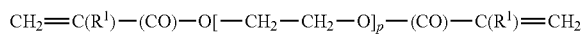

$$CH_2=C(R^1)-(CO)-O[-CH_2-CH_2-O]_p-(CO)-C(R^1)=CH_2 \quad (II)$$

wherein
      the monomer of Formula (II) is not miscible with the first phase;
      p is an integer is no greater than 30;
      $R^1$ is hydrogen or alkyl; and
      2) a poly(propylene glycol) having a weight average molecular weight of at least 500 grams/mole, wherein the poly(propylene glycol) is removed from the polymerized product to provide the porous polymeric core;
b) a biologically active agent positioned within the porous polymeric core, wherein the biologically active agent is not covalently bonded to the porous polymeric core; and
c) a coating layer around the porous polymeric core particle, wherein the coating layer comprises a thermoplastic polymer, a wax, or a mixture thereof.

2. The polymeric composite particle of claim 1, wherein the polymeric composite particle has a core-shell configuration with the core being the porous polymeric core particle and the shell being the coating layer.

3. The polymeric composite particle of claim 1, wherein the first phase comprise water and 10 to 30 weight percent polysaccharide based on a total weight of the first phase.

4. The polymeric composite particle of claim 1, wherein the first phase comprises the compound of Formula (I) and a nonionic surfactant.

5. The polymeric composite particle of claim 1, wherein the monomer composition comprises a second monomer of Formula (III)

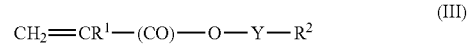

$$CH_2=CR^1-(CO)-O-Y-R^2 \quad (III)$$

wherein
   $R^1$ is hydrogen or methyl;
   Y is a single bond, alkylene, oxyalkylene, or poly(oxyalkylene); and
   $R^2$ is a carbocyclic group or heterocyclic group.

6. The polymeric composite particle of claim 1, wherein the monomer composition comprises a second monomer of Formula (VII) or a salt thereof

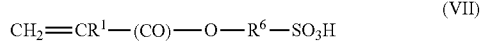

$$CH_2=CR^1-(CO)-O-R^6-SO_3H \quad (VII)$$

wherein
   $R^1$ is hydrogen or methyl; and
   $R^6$ is an alkylene.

7. The polymeric composite particle of claim 1, wherein the biologically active agent comprises a herbicide, insecticide, fungicide, or mixture thereof.

8. The polymeric composite particle of claim 1, wherein the coating layer comprises a silicone-based thermoplastic polymer, (meth)acrylate-based thermoplastic polymer, olefin-based thermoplastic polymer, styrene-based thermoplastic polymer, or a phenoxy-based resin.

9. The polymeric composite particle of claim 1, wherein the coating layer comprises an animal wax, vegetable wax, petroleum wax, hydrogenate vegetable oil, or polyethylene.

10. The polymeric composite particle of claim 1, wherein the polymeric composite particle comprises 20 to 90 weight percent porous polymeric core particle, 0.1 to 40 weight percent biologically active agent, and 10 to 80 weight percent coating layer.

11. A method of delivering a biologically active agent, the method comprising:
providing a polymeric composite particle comprising
   a) a porous polymeric core particle comprising a washed and dried polymerized product of a reaction mixture comprising:
      i) a first phase comprising either
         1) water and a polysaccharide dissolved in the water; or
         2) a surfactant and a compound of Formula (I)

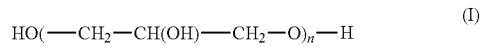

$$HO(-CH_2-CH(OH)-CH_2-O)_n-H \quad (I)$$

ii) a second phase dispersed in the first phase, wherein a volume of the first phase is greater than a volume of the second phase and wherein the second phase comprises
1) a monomer composition comprising a first monomer of Formula (II)

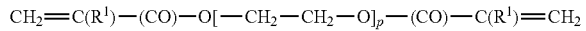

$$CH_2{=}C(R^1){-}(CO){-}O[{-}CH_2{-}CH_2{-}O]_p{-}(CO){-}C(R^1){=}CH_2 \qquad (II)$$

wherein
the monomer of Formula (II) is not miscible with the first phase;
p is an integer is no greater than 30;
$R^1$ is hydrogen or alkyl; and
2) a poly(propylene glycol) having a weight average molecular weight of at least 500 grams/mole,
wherein the poly(propylene glycol) is removed from the polymerized product to provide the porous polymeric core;
b) a biologically active agent positioned within the porous polymeric core, wherein the biologically active agent is not covalently bonded to the porous polymeric core; and
c) a coating layer around the porous polymeric core particle, wherein the coating layer comprises a thermoplastic polymer, a wax, or a mixture thereof; and
releasing the biologically active agent from the polymeric composite particle by diffusion through the coating layer.

12. The method of claim 11, wherein the first phase comprise water and 10 to 30 weight percent polysaccharide based on a total weight of the first phase.

13. The method of claim 11, wherein the first phase comprises the compound of Formula (I) and a nonionic surfactant.

14. The method of claim 11, wherein providing the polymeric composite particle comprises
forming the porous polymeric core particle;
positioning the biologically active agent within the porous polymeric core particle to form a loaded polymeric particle; and
depositing the coating layer around the loaded polymeric particle.

15. The method of claim 14, wherein depositing the coating layer comprises
preparing a coating solution or a coating dispersion;
mixing the loaded polymeric particle with the coating solution or coating dispersion to form a slurry; and
drying the slurry, wherein drying comprises spray drying or fluidized bed drying.

* * * * *

UNITED STATES PATENT AND TRADEMARK OFFICE
CERTIFICATE OF CORRECTION

PATENT NO.        : 10,111,424 B2
APPLICATION NO.   : 14/891560
DATED             : October 30, 2018
INVENTOR(S)       : Hassan Sahouani Page 1 of 1

It is certified that error appears in the above-identified patent and that said Letters Patent is hereby corrected as shown below:

In the Specification

Column 4
Line 17, delete "hdyroxyethyl" and insert -- hydroxyethyl --, therefor.

Column 18
Line 5, delete "vascodilators," and insert -- vasodilators, --, therefor.

Column 22
Line 66, delete "Hunstman" and insert -- Huntsman --, therefor.

Column 23
Line 2, delete "Hunstman" and insert -- Huntsman --, therefor.

Column 26
Line 10, delete "polyoxalkylene" and insert -- polyoxyalkylene --, therefor.

Columns 43-44
Line 33 (approx.), delete "-phenylphosphineooxide," and insert -- -phenylphosphineoxide, --, therefor.

Column 46
Line 12 (approx.), delete "the an" and insert -- an --, therefor.

In the Claims

Column 49
Line 58, in Claim 1, delete "$R^1$is" and insert -- $R^1$ is --, therefor.

Signed and Sealed this
Twenty-fifth Day of December, 2018

Andrei Iancu
*Director of the United States Patent and Trademark Office*